US012746221B2

(12) United States Patent
Zhai et al.

(10) Patent No.: US 12,746,221 B2
(45) Date of Patent: Sep. 29, 2026

(54) COMBINATIONS OF BCL-2/BCL-XL INHIBITORS AND RELATED USES

(71) Applicants: Ascentage Pharma (Suzhou) Co., Ltd., Suzhou (CN); Ascentage Pharma Group Corp Limited, Hong Kong (CN)

(72) Inventors: Yifan Zhai, Suzhou (CN); Dajun Yang, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 1099 days.

(21) Appl. No.: 17/428,692

(22) PCT Filed: Apr. 1, 2021

(86) PCT No.: PCT/CN2021/084970

§ 371 (c)(1),
(2) Date: Aug. 5, 2021

(87) PCT Pub. No.: WO2021/204060

PCT Pub. Date: Oct. 14, 2021

(65) Prior Publication Data

US 2022/0296557 A1 Sep. 22, 2022

(30) Foreign Application Priority Data

Apr. 10, 2020 (WO) ................ PCT/CN2020/084145
Mar. 31, 2021 (CN) ......................... 202110344288.4

(51) Int. Cl.

*A61P 35/00* (2006.01)
*A61K 31/337* (2006.01)
*A61K 31/506* (2006.01)
*A61K 31/519* (2006.01)
*A61K 45/06* (2006.01)

(52) U.S. Cl.

CPC .......... *A61K 31/337* (2013.01); *A61K 31/506* (2013.01); *A61K 31/519* (2013.01); *A61K 45/06* (2013.01); *A61P 35/00* (2018.01)

(58) Field of Classification Search

CPC .. A61K 31/337; A61K 31/506; A61K 31/519; A61P 35/00

See application file for complete search history.

(56) References Cited

U.S. PATENT DOCUMENTS 11,491,168 B2 11/2022 Zhai et al.
12,083,136 B2 9/2024 Yang et al.
2014/0199234 A1 * 7/2014 Wang .................. A61K 31/496 424/93.73
2020/0297743 A1 9/2020 Zhai et al.
2023/0025865 A1 * 1/2023 Sun ...................... A61K 31/337
2024/0390401 A1 11/2024 Yang et al.

FOREIGN PATENT DOCUMENTS

WO WO-2012103059 A2 8/2012
WO WO-2014113413 A1 7/2014
WO WO-2016127135 A1 * 8/2016 ........... A61K 31/496
WO WO-2019089991 A1 * 5/2019 ........... A61K 31/337
WO WO-2020024932 A1 2/2020
WO WO-2020024976 A1 2/2020
WO WO-2021204060 A1 10/2021

OTHER PUBLICATIONS

Rautio, J.; et al. "The expanding role of prodrugs in contemporary drug design and development" 2018, Nat. Rev. Drug Discovery, vol. 17, pp. 559-587. (Year: 2018).*
Wellmer, A.; et al. "Experimental Pneumococcal Meningitis: Impaired Clearance of Bacteria from the Blood Due to Increased Apoptosis in the Spleen in Bcl-2-Deficient Mice" 2004, Infection and Immunity, vol. 72, pp. 3113-3119. (Year: 2004).*
Wu, Y.; et al. "A Phase I Study of Novel Bcl-2/Bcl-XL Inhibitor APG-1252 in Patients with Advanced SCLC or Other Solid Tumor" 2018, Journal of Thoracic Oncology, vol. 13, pp. S1048-S1049, OA12. (Year: 2018).*
Wang, H.; et al. "Preclinical studies of a dual Bcl-2/Bcl-xL inhibitor APG-1252 with strong anti-tumor efficacy and significantly reduced platelet toxicity" 2014, European Journal of Cancer, pp. 176-177, Abstract 544. (Year: 2014).*
Shi, J et al. "Navitoclax (ABT-263) Accelerates Apoptosis during Drug-Induced Mitotic Arrest by Antagonizing Bcl-xL" 2011, Cancer Research, vol. 71, pp. 4518-4526. (Year: 2011).*
NCT03080311 clinical trial information (record updated Jul. 11, 2018). (Year: 2018).*
Marchetti, P .; et al. "Weekly administration of paclitaxel: theoretical and clinical basis" 2002, Critical Reviews in Oncology Hematology, vol. 44, pp. S3-S13. (Year: 2002).*
Skoulidis, F .; et al. "Targeting the Gatekeeper: Osimertinib in Egfr T790M Mutation-Positive Non-Small Cell Lung Cancer" 2017, Clinical Cancer Research 2017, vol. 23, pp. 618-622. (Year: 2017).*
Hata, A. N.; et al. "Tumor cells can follow distinct evolutionary paths to become resistant to epidermal growth factor receptor inhibition" 2016, Nature Medicine, vol. 22, pp. 262-269. (Year: 2016).*
Label information of the pharmaceutical "Tagrisso" (revised Aug. 2018). (Year: 2018).*
Harrison, C. N.; et al. "Results from a Phase 2 Study of Navitoclax in Combination with Ruxolitinib in Patients with Primary or Secondary Myelofibrosis" 2019, Blood, vol. 134, Supplement_1: 671. (Year: 2019).*

(Continued)

*Primary Examiner* — Andrea Olson
*Assistant Examiner* — Benjamin M Brandsen
(74) *Attorney, Agent, or Firm* — Goodwin Procter LLP

(57) ABSTRACT

The present disclosure relates to combinations of Compound No. 1 or a pharmaceutically acceptable salt thereof and at least one additional therapeutic agent. The present disclosure also relates to methods of treating or preventing a disease via administering to subjects in need thereof Compound No. 1 or a pharmaceutically acceptable salt thereof and at least one additional therapeutic agent.

7 Claims, 6 Drawing Sheets

(56) References Cited

OTHER PUBLICATIONS

Yi, C. A.; et al. Efficacy and Safety of Ruxolitinib in the Treatment of Patients with Myelofibrosis 2015, Future Oncology, vol. 11, p. 719-733. (Year: 2015).*
Perimenis, P.; et al. "IAP antagonists Birinapant and AT-406 efficiently synergise with either TRAIL, BRAF, or BCL-2 inhibitors to sensitise BRAFV600E colorectal tumour cells to" 2016, BMC Cancer, vol. 16, article 624. (Year: 2016).*
Morrish, E.; et al. "Future Therapeutic Directions for Smac-Mimetics" 2020, Cells, vol. 9, article 406. (Year: 2020).*
Xu, R.; et al. "A phase I study of a novel IAP inhibitor APG-1387 in patients with advanced solid tumors" 2018, Journal of Clinical Oncology, vol. 36, No. 15 Supplement. (Year: 2018).*
International Search Report and Written Opinion, mailed Jun. 29, 2021, for International Application No. PCT/CN2021/084970 (12 total pages).
Laptrinhx/News: "Ascentage Pharma to Present the Latest Results from Six Preclinical Studies at AACR Annual Meeting 2021," LaptrinhX/News, Retrieved from the Internet at https://laptrinhx.com/news/ascentage-pharma-to-present-the-latest-results-from-six-preclinical-studies-at-aacr-annual-meeting-2021-BYDkqN/; Retrieved on Sep. 27, 2022 (Mar. 2021).
NCT04210037: Study of Combination APG-1252 Plus Paclitaxel in Patients with Relapsed/Refractry Small Cell Lung Cancer, Retrieved from the Internet at https://clinicaltrials.gov/ct2/history/NCT04210037?V_1=View#StudyPageTop, Retrieved on Sep. 27, 2022 (Dec. 2019) (6 total pages).
Partial Supplementary European Search Report, dated Feb. 15, 2022, for EP Application No. 21754882.5 (15 total pages).
Karjalainen, R., et al., "JAK1/2 and BCL2 inhibitors synergize to counteract bone marrow stromal cell-induced protection of AML," Blood, Aug. 10, 2017, vol. 130, No. 6, pp. 789-802.
Waibel, M., et al., Combined Targeting of JAK2 and Bcl-2/Bcl-xL to Cure Mutant JAK2-Driven Malignancies and Overcome Acquired Resistance to JAK2 Inhibitors, Cell Reports 5, Nov. 27, 2013, pp. 1047-1059.
Will, B., et al., "Apoptosis induced by JAK2 inhibition is mediated by Bim and enhanced by the BH3 mimeticABT-737 in JAK2 mutant human erythroid cells," Blood, Apr. 8, 2010, vol. 115, No. 14, pp. 2901-2909.
NCT04001777: "A Study of APG-1252 Plus Osimertinib (AZD9291) in EGFR TKI Resistant NSCLC Patients," Jul. 17, 2019, version number (2); Retrieved from the Internet at https://clinicaltrials.gov/study/NCT04001777?tab=history&a=2#document-section-card, Retrieved on Feb. 12, 2025, 11 pages.
Office Action, dated Feb. 15, 2022, for Taiwan Patent Application No. 110112218, 10 pages (w/ English machine translation).
Shoji, S., et al., "First-line osimertinib treatment in patients with lung squamous cell carcinoma harboring active epidermal growth factor receptor mutations," Lung Cancer, 2020, vol. 140, pp. 113-115.
Zhang, L., et al., "Phase 1b Study of Pelcitoclax (APG-1252) in Combination with Osimertinib in Patients with EGFR TKI Resistant NSCLC," Abstract MA02.06, Abstracts, Oct. 2021, S891.
Zhang, L., et al., Updated study results of pelcitoclax (APG-1252) in combination with osimertinib in patients (pts) with EGFR-mutant non-small cell lung cancer (NSCLC), J Clin Oncol, 40: 9116-9116 (2022).

* cited by examiner

COMBINATIONS OF BCL-2/BCL-XL INHIBITORS AND RELATED USES

RELATED APPLICATIONS

This application is a U.S. National Phase application, filed under 35 U.S.C. § 371 (c), of International Application No. PCT/CN2021/084970, filed Apr. 1, 2021, which claims priority to, and the benefit of, International Application No. PCT/CN2020/084145, filed Apr. 10, 2020, and Chinese Application No. 202110344288.4, filed Mar. 31, 2021, the contents of each of which are incorporated by reference herein in their entireties.

BACKGROUND

Apoptosis is a natural pathway for the body to clear abnormal or unwanted cells, and if it is affected, it may lead to various diseases such as cancer. Bcl-2 family proteins are important regulators of apoptosis. The family of proteins includes anti-apoptotic proteins such as Bcl-2, Bcl-xL and Mcl-1, and pro-apoptotic molecules including Bid, Bim, Bad, Bak and Bax. Although normal cells have low expression levels of anti-apoptotic Bcl-2 and Bcl-xL proteins, these proteins are found to be highly overexpressed in many different types of human tumors and are implied in tumor development, progression and resistance to drugs. There exists a need for a combination of: (1) a Bcl-2/Bcl-xL inhibitor having high anti-cancer activity and/or low side effects, and (2) at least one additional therapeutic agent. The present disclosure addresses the need.

Neuroendocrine tumors (NETs) are neoplasms that arise from cells of the endocrine (hormonal) and nervous systems. Current targeted therapies extend progression-free survival (PFS) in patients with G1 or G2 neuroendocrine tumors (NET), but the objective response rate remains low. Hence, more effective therapy is needed to improve clinical outcomes. The present disclosure addresses the need.

SUMMARY

In some aspects, the present disclosure provides a combination comprising:

(i) a pharmaceutically effective amount of Compound No. 1 or a pharmaceutically acceptable salt thereof; and (ii) at least one additional therapeutic agent.

In some aspects, the present disclosure provides a pharmaceutical composition comprising a combination disclosed herein and one or more pharmaceutically acceptable carriers or excipients.

In some aspects, the present disclosure provides a pharmaceutical kit comprising a combination disclosed herein.

In some aspects, the present disclosure provides a method of treating or preventing a disease in a subject, comprising administering to the subject:

(i) a pharmaceutically effective amount of Compound No. 1 or a pharmaceutically acceptable salt thereof, and (ii) at least one additional therapeutic agent.

In some aspects, the present disclosure provides a combination for treating or preventing a disease in a subject, wherein the combination comprises:

(i) a pharmaceutically effective amount of Compound No. 1 or a pharmaceutically acceptable salt thereof; and (ii) at least one additional therapeutic agent.

In some aspects, the present disclosure provides use of a combination in the manufacture of a medicament for treating or preventing a disease in a subject, wherein the combination comprises:

(i) a pharmaceutically effective amount of Compound No. 1 or a pharmaceutically acceptable salt thereof; and (ii) at least one additional therapeutic agent.

In some aspects, the present disclosure provides a combination comprising:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a method of treating or preventing cancer (e.g., SCLC (e.g., relapsed and/or refractory SCLC)) in a subject, comprising administering to the subject:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a combination for treating or preventing cancer (e.g., SCLC (e.g., relapsed and/or refractory SCLC)) in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable so salt thereof.

In some aspects, the present disclosure provides use of a combination in the manufacture of a medicament for treating or preventing cancer (e.g., SCLC (e.g., relapsed and/or refractory SCLC)) in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides a method of treating or preventing cancer (e.g., NSCLC (e.g., EGFR-TKI-resistant NSCLC)) in a subject, comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a combination for treating or preventing cancer (e.g., NSCLC (e.g., EGFR-TKI-resistant NSCLC)) in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides use of a combination in the manufacture of a medicament for treating or preventing cancer (e.g., NSCLC (e.g., EGFR-TKI-resistant NSCLC)) in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides a method of treating or preventing cancer (e.g., NSCLC) in a subject, wherein the cancer (e.g., NSCLC) is resistant to treatment with osimertinib or a pharmaceutically acceptable salt thereof alone, the method comprising administering to the subject:

(i) a pharmaceutically effective amount of Compound No. 1 or a pharmaceutically acceptable salt thereof; and
(ii) a pharmaceutically effective amount of osimertinib or a pharmaceutically acceptable salt thereof (e.g., a mesylate salt of osimertinib).

In some aspects, the present disclosure provides a combination for treating or preventing cancer (e.g., NSCLC) in a subject, wherein the cancer (e.g., NSCLC) is resistant to treatment with osimertinib or a pharmaceutically acceptable salt thereof alone, the combination comprising:

(i) a pharmaceutically effective amount of Compound No. 1 or a pharmaceutically acceptable salt thereof; and
(ii) a pharmaceutically effective amount of osimertinib or a pharmaceutically acceptable salt thereof.

In some aspects, the present disclosure provides use of a combination in the manufacture of a medicament for treating or preventing cancer (e.g., NSCLC) in a subject, wherein the cancer (e.g., NSCLC) is resistant to treatment with osimertinib or a pharmaceutically acceptable salt thereof alone, the combination comprising:

(i) a pharmaceutically effective amount of Compound No. 1 or a pharmaceutically acceptable salt thereof; and
(ii) a pharmaceutically effective amount of osimertinib or a pharmaceutically acceptable salt thereof.

In some aspects, the present disclosure provides a method of treating or preventing cancer in a subject, wherein an EGFR mutation (e.g., G719X, S768I, L861Q, L747P, an exon 19 insertion, an exon 20 insertion, T790M, V843I, or any combination thereof) is identified in the subject (e.g., in a biological sample from the subject), comprising administering to the subject:

(i) a pharmaceutically effective amount of Compound No. 1 or a pharmaceutically acceptable salt thereof; and
(ii) a pharmaceutically effective amount of osimertinib or a pharmaceutically acceptable salt thereof (e.g., a mesylate salt of osimertinib).

In some aspects, the present disclosure provides a method of treating or preventing cancer in a subject, comprising:

(a) identifying the presence of an EGFR mutation (e.g., G719X, S768I, L861Q, L747P, an exon 19 insertion, an exon 20 insertion, T790M, V843I, or any combination thereof) in the subject (e.g., in a biological sample from the subject); and
(b) administering to the subject:
    (i) a pharmaceutically effective amount of Compound No. 1 or a pharmaceutically acceptable salt thereof; and
    (ii) a pharmaceutically effective amount of osimertinib or a pharmaceutically acceptable salt thereof (e.g., a mesylate salt of osimertinib).

In some aspects, the present disclosure provides a method of treating or preventing a disease (e.g., neuroendocrine neoplasm (NEN)) in a subject, comprising administering to the subject a pharmaceutically effective amount of Compound No. 1 or Compound No. 2 or a pharmaceutically acceptable salt thereof.

In some aspects, the present disclosure provides Compound No. 1 or Compound No. 2 or a pharmaceutically acceptable salt thereof for treating or preventing a disease (e.g., neuroendocrine neoplasm (NEN)) in a subject.

In some aspects, the present disclosure provides use of Compound No. 1 or Compound No. 2 or a pharmaceutically acceptable salt thereof in the manufacture of a medicament for treating or preventing a disease (e.g., neuroendocrine neoplasm (NEN)) in a subject.

In some aspects, the present disclosure provides Compound No. 1 or a pharmaceutically acceptable salt thereof for use in combination with at least one additional therapeutic agent (e.g., paclitaxel, osimertinib, ruxolitinib, Compound A, or a pharmaceutically acceptable salt thereof) in treating or preventing a disease in a subject.

In some aspects, the present disclosure provides at least one additional therapeutic agent (e.g., paclitaxel, osimertinib, ruxolitinib, Compound A, or a pharmaceutically acceptable salt thereof) for use in combination with Compound No. 1 or a pharmaceutically acceptable salt thereof in treating or preventing a disease in a subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions will control. In addition, the materials methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTIONS OF FIGURES

(FIG. 4A: BCL-xL:BIM complex, FIG. 4B: BCL-xL:PUMA complex; and FIG. 4C: BAX:BAK protein complexes).

(FIGS. 5A-5C: BCL-xL and MCL-1 complexes; and FIGS. 6A-6C: correlations between protein complexes and $IC_{50}$).

DETAILED DESCRIPTION

Figure 1:
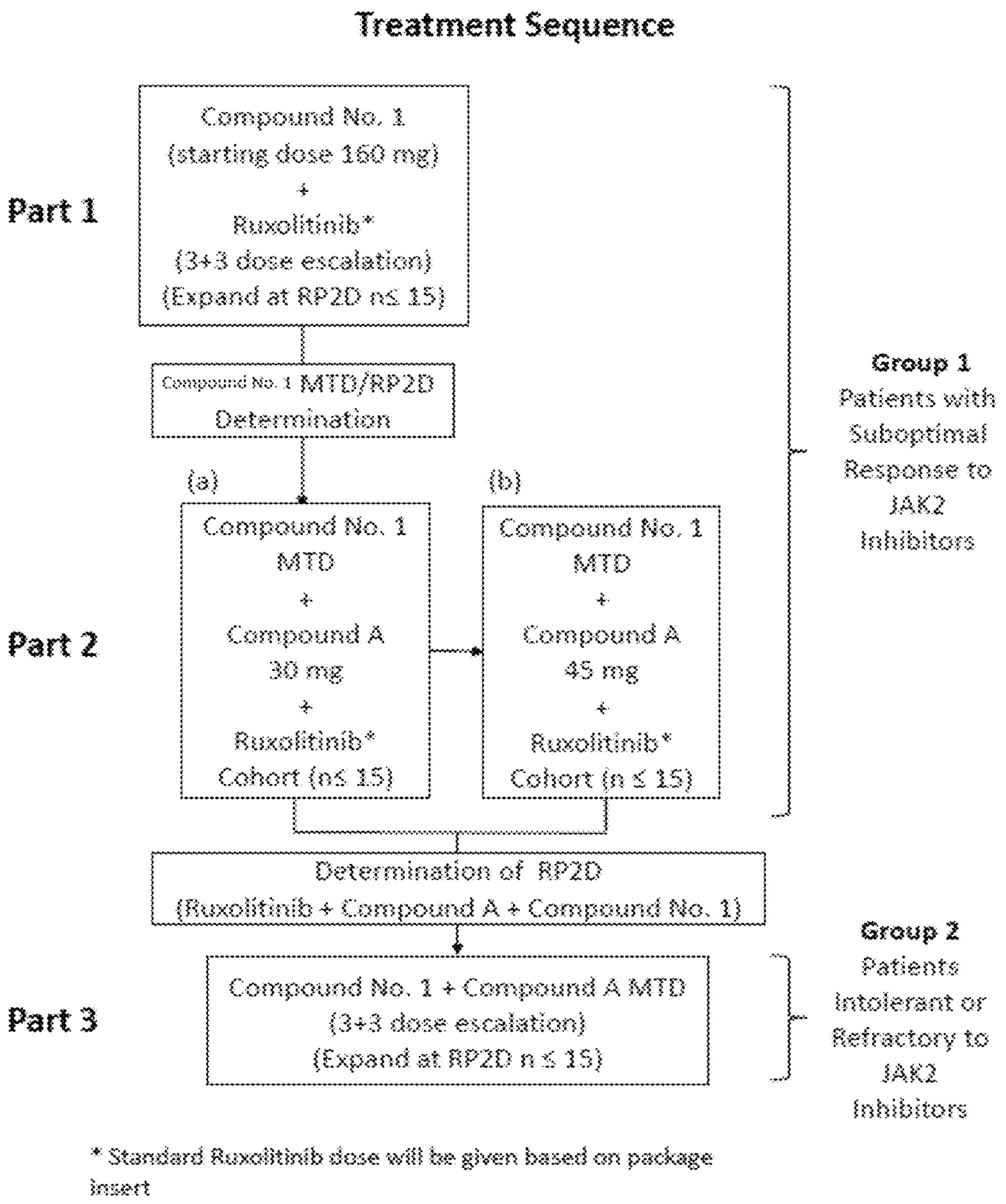
FIG. 1 is a schematic diagram showing the design of the study of combination of Compound No. 1 with ruxolitinib and/or Compound A in patients with myelofibrosis.

It is understood that the term "Compound No. 1," as used herein, refers to a compound having the following structure:

(Compound No. 1)

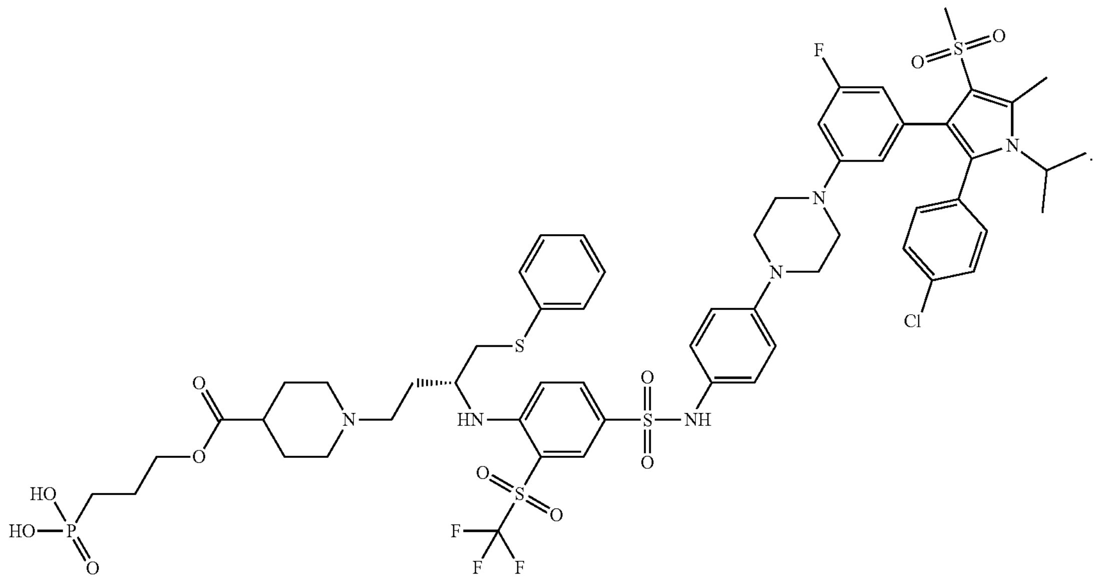

Compound No. 1 may be identified by the IUPAC name of (3R)-1-(3-(4-(4-(4-(3-(2-(4-chlorophenyl)-1-isopropyl-4-methylsulfonyl-5-methyl-1H-pyrrol-3-yl)-5-fluorophenyl) piperazin-1-yl)-phenylaminosulfonyl)-2-trifluoromethyl-sulfonyl-anilino)-4-phenylthio-butyl)-piperidine-4-carboxylic acid 3-phosphonopropyl ester.

It is understood that the term "Compound No. 2," as used herein, refers to a compound having the following structure:

(Compound No. 2)

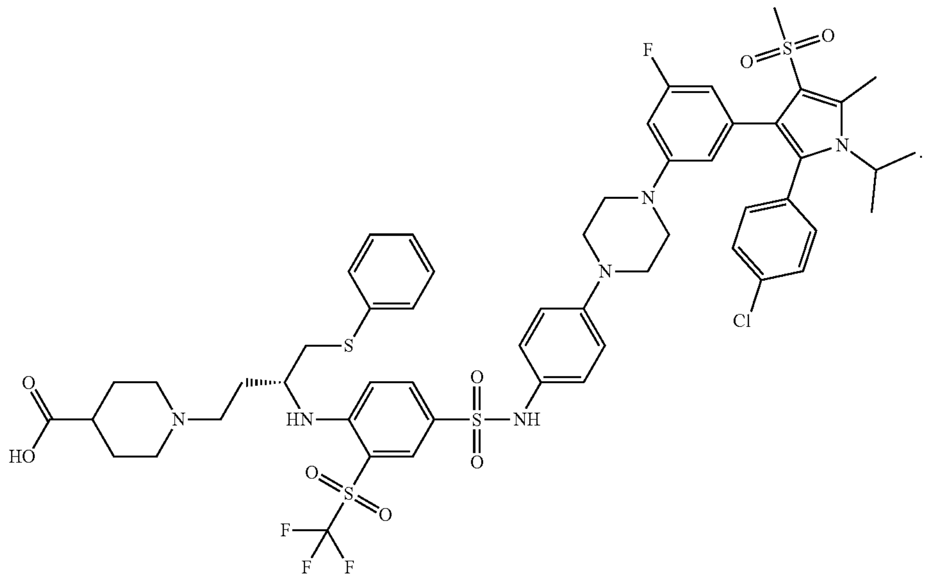

Compound No. 2 may be identified by the IUPAC name of ((R)-1-(3-((4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((trifluoromethyl)sulfonyl)phenyl)amino)-4-(phenylthio)butyl)piperidine-4-carboxylic acid.

Without wishing to be bound by theory, it is understood that Compound No. 1 may be used as a prodrug of Compound No. 2 in some embodiments of combinations, methods, and uses described herein.

Without wishing to be bound by theory, it is understood that Compound No. 2 may be a metabolite of Compound No. 1 in some embodiments of combinations, methods, and uses described herein.

It is understood that the term "paclitaxel", as used herein, refers to a compound having the following structure:

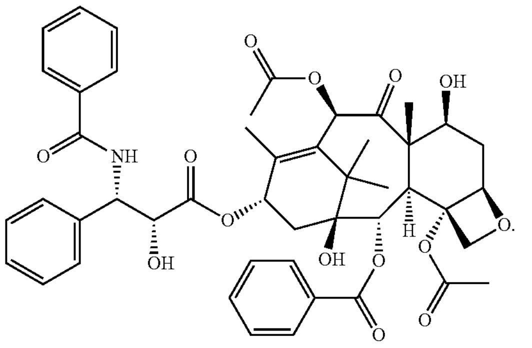

(Paclitaxel)

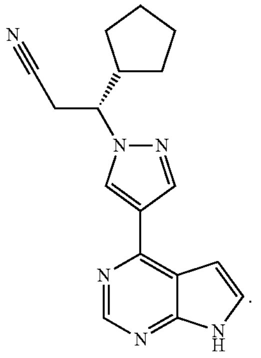

(Ruxolitinib)

Paclitaxel may, be identified by the CAS No. 33069-62-4 and/or by the IUPAC name of (2α,4α,5β,7β,10β,13α)-4,10-Bis(acetyloxy)-13-1{[(2R,3S)-3-(benzoylamino)-2-hydroxy-3-phenylpropanoyl]oxy}-1,7-dihydroxy-9-oxo-5,20-epoxytax-11-en-2-yl benzoate. In some embodiments, paclitaxel is sold under the trademark TAXOL®.

It is understood that the term "osimertinib", as used herein, refers to a compound having the following structure:

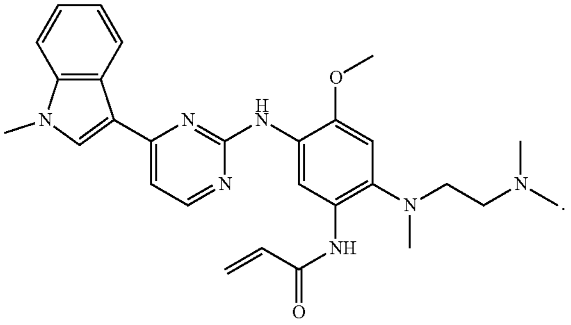

(Osimertinib)

Ruxolitinib may be identified by the CAS No. 941678-49-5 and/or by the IUPAC name of (3R)-3-Cyclopentyl-3-[4-(7H-pyrrolo[2,3-d]pyrimidin-4-yl)pyrazol-1-yl]propanenitrile. In some embodiments, ruxolitinib is sold under the trademark JAKAFI It is understood that the term "Compound A," as used herein, refers to a compound having the following structure:

(Compound A)

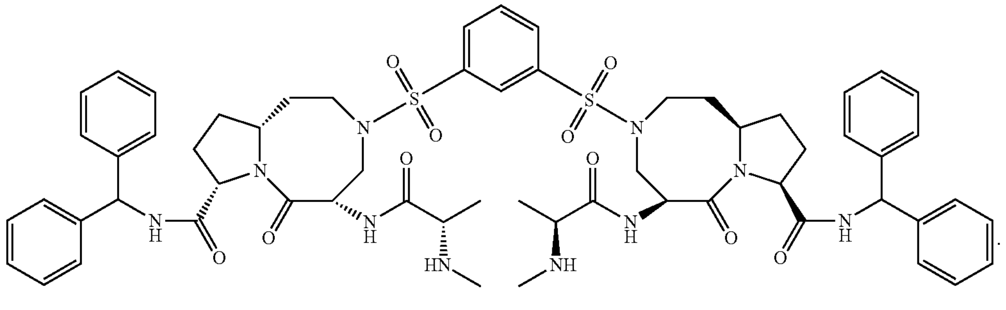

Osimertinib may be identified by code AZD9291, by the CAS No. 1421373-65-0, and/or by the IUPAC name of N-(2-{2-dimethylaminoethyl-methylamino}-4-methoxy-5-{[4-(1-methylindol-3-yl)pyrimidin-2-yl]amino}phenyl)prop-2-enamide. In some embodiments, osimertinib is sold under the trademark TAGRISSO®.

It is understood that the term "ruxolitinib", as used herein, refers to a compound having the following structure:

Compound No. 1 may be identified by the IUPAC name of ((5S,5'S,8S,8'S, 10aR,10'R)-3,3'-(1,3-phenylenedisulfonyl)bis(N-benzhydryl-5-((S)-2-(methylamino)propanamido)-6-oxodecahydropyrrolo[1,2-a][1,5]diazocine-8-carboxamide).

It is understood that the term "fedratinib", as used herein, refers to a compound having the following structure:

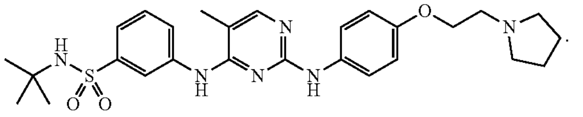

(Fedratinib)

Fedratinib may be identified by the CAS No. 936091-26-8 and/or by the IUPAC name of N-tert-Butyl-3-{5-methyl-2-[4-(2-pyrrolidin-1-yl-ethoxy)-phenylamino]-pyrimidin-4-ylamino}-benzenesulfonamide. In some embodiments, fedratinib is sold under the trademark INREBIC®.

It is understood that the term "navitoclax", as used herein, refers to a compound having the following structure:

In some aspects, the present disclosure provides use of a combination in the manufacture of a medicament for treating or preventing a disease in a subject, wherein the combination comprises:

(i) a pharmaceutically effective amount of Compound No. 1 or a pharmaceutically acceptable salt thereof; and (ii) at least one additional therapeutic agent (e.g., paclitaxel, osimertinib, ruxolitinib, Compound A, or a pharmaceutically acceptable salt thereof).

In some aspects, the present disclosure provides Compound No. 1 or a pharmaceutically acceptable salt thereof for use in combination with at least one additional therapeutic agent (e.g., paclitaxel, osimertinib, ruxolitinib, Compound A. or a pharmaceutically acceptable salt thereof) in treating or preventing a disease in a subject.

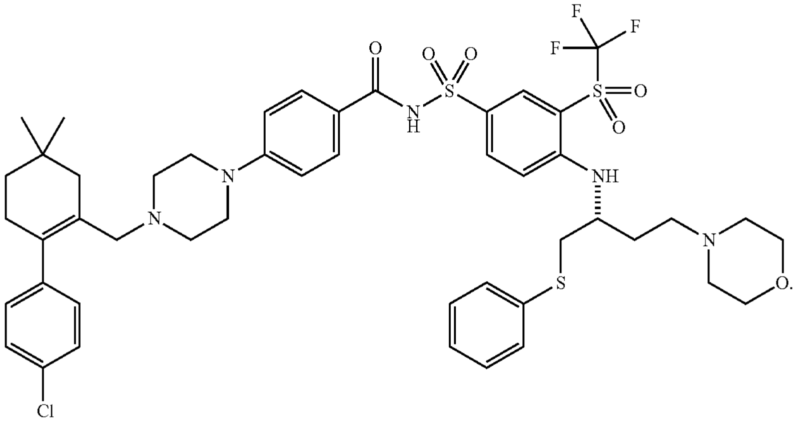

(Navitoclax)

Navitoclax may be identified code ABT-263, by the CAS No. 923564-51-6, and/or by the IUPAC name of 4-(4-{[2-(4-Chlorophenyl)-5,5-dimethyl-1-cyclohexen-1-yl] methyl}-1-piperazinyl)-N-[(4-{[(R)-4-(4-morpholinyl)-1-(phenylsulfanyl)-2-butanyl]amino}-3-[(trifluoromethyl) sulfonyl]phenyl)-sulfonyl]benzamide.

Combinations, Methods, and Uses of the Present Disclosure

In some aspects, the present disclosure provides a combination comprising:

(i) a pharmaceutically effective amount of Compound No. 1 or a pharmaceutically acceptable salt thereof; and (ii) at least one additional therapeutic agent (e.g., paclitaxel, osimertinib, ruxolitinib, Compound A, or a pharmaceutically acceptable salt thereof).

In some aspects, the present disclosure provides a method of treating or preventing a disease in a subject, comprising administering to the subject:

(i) a pharmaceutically effective amount of Compound No. 1 or a pharmaceutically acceptable salt thereof; and (ii) at least one additional therapeutic agent (e.g., paclitaxel, osimertinib, ruxolitinib, Compound A, or a pharmaceutically acceptable salt thereof).

In some aspects, the present disclosure provides a combination for treating or preventing a disease in a subject, wherein the combination comprises:

(i) a pharmaceutically effective amount of Compound No. 1 or a pharmaceutically acceptable salt thereof; and (ii) at least one additional therapeutic agent (e.g., paclitaxel, osimertinib, ruxolitinib, Compound A. or a pharmaceutically acceptable salt thereof).

In some aspects, the present disclosure provides at least one additional therapeutic agent (e.g., paclitaxel, osimertinib, ruxolitinib, Compound A, or a pharmaceutically acceptable salt thereof) for use in combination with Compound No. 1 or a pharmaceutically acceptable salt thereof in treating or preventing a disease in a subject.

In some aspects, the present disclosure provides a method of treating or preventing a disease (e.g., neuroendocrine neoplasm (NEN)) in a subject, comprising administering to the subject a pharmaceutically effective amount of Compound No. 1 or Compound No. 2 or a pharmaceutically acceptable salt thereof.

In some aspects, the present disclosure provides Compound No. 1 or Compound No. 2 or a pharmaceutically acceptable salt thereof for treating or preventing a disease (e.g., neuroendocrine neoplasm (NEN)) in a subject.

In some aspects, the present disclosure provides use of Compound No. 1 or Compound No. 2 or a pharmaceutically acceptable salt thereof in the manufacture of a medicament for treating or preventing a disease (e.g., neuroendocrine neoplasm (NEN)) in a subject.

In some embodiments, Compound No. 1 is administered to the subject.

In some embodiments, a pharmaceutically acceptable salt of Compound No. 1 is administered to the subject.

In some embodiments, the at least one additional therapeutic agent comprises paclitaxel, osinertinib, ruxolitinib, Compound A, a pharmaceutically acceptable salt thereof, a prodrug thereof, or any combination thereof.

In some embodiments, the at least one additional therapeutic agent comprises paclitaxel, a pharmaceutically acceptable salt thereof, or a prodrug thereof.

In some embodiments, the at least one additional therapeutic agent comprises paclitaxel.

In some embodiments, the at least one additional therapeutic agent comprises a pharmaceutically acceptable salt of paclitaxel.

In some embodiments, the at least one additional therapeutic agent comprises a prodrug of paclitaxel.

In some embodiments, the at least one additional therapeutic agent comprises osimertinib, a pharmaceutically acceptable salt thereof, or a prodrug thereof.

In some embodiments, the at least one additional therapeutic agent comprises osimertinib.

In some embodiments, the at least one additional therapeutic agent comprises a pharmaceutically acceptable salt of osimertinib (e.g., a mesylate salt of osimertinib).

In some embodiments, the at least one additional therapeutic agent comprises a prodrug of osimertinib.

In some embodiments, the at least one additional therapeutic agent comprises at least one Janus kinase (JAK) inhibitor.

In some embodiments, the JAK inhibitor is an inhibitor of JAK1, JAK2, JAK3, or any combination thereof.

In some embodiments, the JAK inhibitor is a selective inhibitor of JAK1 and/or JAK2.

In some embodiments, the JAK inhibitor is a selective inhibitor of JAK1.

In some embodiments, the JAK inhibitor is a selective inhibitor of JAK2.

In some embodiments, the at least one additional therapeutic agent comprises ruxolitinib, a pharmaceutically acceptable salt thereof, or a prodrug thereof.

In some embodiments, the at least one additional therapeutic agent comprises ruxolitinib.

In some embodiments, the at least one additional therapeutic agent comprises a pharmaceutically acceptable salt of ruxolitinib.

In some embodiments, the at least one additional therapeutic agent comprises a prodrug of ruxolitinib.

In some embodiments, the at least one additional therapeutic agent comprises Compound A, a pharmaceutically acceptable salt thereof, or a prodrug thereof.

In some embodiments, the at least one additional therapeutic agent comprises Compound A.

In some embodiments, the at least one additional therapeutic agent comprises a pharmaceutically acceptable salt of Compound A.

In some embodiments, the at least one additional therapeutic agent comprises a prodrug of Compound A.

In some embodiments, the at least one additional therapeutic agent comprises a JAK inhibitor, and Compound A, a pharmaceutically acceptable salt thereof, or a prodrug thereof.

In some embodiments, the at least one additional therapeutic agent comprises:

(ii-a) ruxolitinib, a pharmaceutically acceptable salt thereof, or a prodrug thereof; and (ii-b) Compound A, a pharmaceutically acceptable salt thereof, or a prodrug thereof.

In some embodiments, the at least one additional therapeutic agent comprises:

(ii-a) ruxolitinib or a pharmaceutically acceptable salt thereof; and (ii-b) Compound A or a pharmaceutically acceptable salt thereof.

In some embodiments, the at least one additional therapeutic agent comprises ruxolitinib and Compound A.

Suitable Subjects and Diseases

In some embodiments, the subject is a mammal.

In some embodiments, the subject is a human.

In some embodiments, the subject is a human at the age of about 18 years or older.

In some embodiments, the subject is a human at the age of younger than 18 years.

In some embodiments, the disease is cancer.

In some embodiments, the disease is relapsed and/or refractory cancer.

In some embodiments, the disease is EGFR-TKI-resistant cancer.

In some embodiments, the disease is cancer resistant to treatment with osimertinib or a pharmaceutically acceptable salt thereof, but without Compound No. 1 or a pharmaceutically acceptable salt thereof.

In some embodiments, the disease is cancer resistant to treatment with osimertinib or a pharmaceutically acceptable salt thereof alone.

In some embodiments, the disease is cancer resistant to a platinum-based chemotherapy and/or an immunotherapy.

In some embodiments, the platinum-based chemotherapy comprises cisplatin (CDDP), carboplatin (CBDCA), nedaplatin (CDGP), or any combination thereof. In some embodiments, the platinum-based chemotherapy further comprises bevacizumab (BEV).

In some embodiments, the disease is small cell lung cancer (SCLC), non-small cell lung carcinoma (NSCLC), or bone marrow cancer (e.g., myelofibrosis).

In some embodiments, the disease is SCLC.

In some embodiments, the disease is relapsed and/or refractory SCLC.

In some embodiments, the disease is EGFR-TKI-resistant SCLC.

In some embodiments, the disease is SCLC resistant to treatment with osimertinib or a pharmaceutically acceptable salt thereof, but without Compound No. 1 or a pharmaceutically acceptable salt thereof.

In some embodiments, the disease is SCLC resistant to treatment with osimertinib or a pharmaceutically acceptable salt thereof alone.

In some embodiments, the disease is SCLC resistant to a platinum-based chemotherapy and/or an immunotherapy.

In some embodiments, the disease is non-small cell lung carcinoma (NSCLC).

In some embodiments, the disease is relapsed and/or refractory NSCLC.

In some embodiments, the disease is EGFR-TKI-resistant NSCLC.

In some embodiments, the disease is NSCLC resistant to treatment with osimertinib or a pharmaceutically acceptable salt thereof, but without Compound No. 1 or a pharmaceutically acceptable salt thereof.

In some embodiments, the disease is NSCLC resistant to treatment with osimertinib or pharmaceutically acceptable salt thereof alone.

In some embodiments, the disease is NSCLC resistant to a platinum-based chemotherapy and/or an immunotherapy.

In some embodiments, the cancer (e.g., NSCLC) is associated with an EGFR mutation (e.g., G719X, S768I, L861Q, L747P, an exon 19 insertion, an exon 20 insertion, T790M, V843I, or any combination thereof).

In some embodiments, the disease is bone marrow cancer.

In some embodiments, the disease is myelofibrosis.

In some embodiments, the disease is relapsed and/or refractory myelofibrosis.

In some embodiments, the disease is myelofibrosis resistant to treatment with ruxolitinib or a pharmaceutically acceptable salt thereof, but without Compound No. 1 or a pharmaceutically acceptable salt thereof.

In some embodiments, the disease is myelofibrosis resistant to treatment with ruxolitinib or a pharmaceutically acceptable salt thereof alone.

In some embodiments, the disease is myelofibrosis resistant to treatment with fedratinib or a pharmaceutically acceptable salt thereof, but without Compound No. 1 or a pharmaceutically acceptable salt thereof.

In some embodiments, the disease is myelofibrosis resistant to treatment with fedratinib or a pharmaceutically acceptable salt thereof alone.

In some embodiments, the cancer (e.g., myelofibrosis) is associated with a JAK mutation (e.g., V617F).

In some embodiments, the disease is neuroendocrine neoplasm (NEN).

In some embodiments, the neuroendocrine neoplasm is G1, G2, or G3 neuroendocrine neoplasm, as classified in Table 1.

In some embodiments, the neuroendocrine neoplasm is G1 or G2 neuroendocrine neoplasm.

In some embodiments, the neuroendocrine neoplasm is G1 neuroendocrine neoplasm.

In some embodiments, the neuroendocrine neoplasm is G2 neuroendocrine neoplasm.

In some embodiments, the neuroendocrine neoplasm is G3 neuroendocrine neoplasm.

In some embodiments, the neuroendocrine neoplasm is neuroendocrine tumor (NET).

In some embodiments, the neuroendocrine neoplasm is G1 neuroendocrine tumor.

In some embodiments, the neuroendocrine neoplasm is G2 neuroendocrine tumor.

In some embodiments, the neuroendocrine neoplasm is neuroendocrine carcinoma (NEC).

TABLE 1

| Grade | Mitotic Count (per 10 HPF) | Ki-67 index (%) |
|---|---|---|
| G1 | <2 | <3% |
| G2 | 2 to 20 | 3-20% |
| G3 | >20 | >20% |

It is understood that 01 and G2 neuroendocrine neoplasms are called neuroendocrine tumors (NETs), and that G3 neuroendocrine neoplasms are called neuroendocrine carcinomas (NECs).

Administrations of Compound No. 1

In some embodiments, Compound No. 1 or the pharmaceutically acceptable salt thereof is administered by enteral administration.

In some embodiments, Compound No. 1 or the pharmaceutically acceptable salt thereof is administered by oral administration.

In some embodiments, Compound No. 1 or the pharmaceutically acceptable salt thereof is administered by parenteral administration.

In some embodiments, Compound No. 1 or the pharmaceutically acceptable salt thereof is administered by intravenous administration.

In some embodiments, Compound No. 1 or the pharmaceutically acceptable salt thereof is administered once weekly.

In some embodiments, Compound No. 1 or the pharmaceutically acceptable salt thereof is administered twice weekly.

In some embodiments, Compound No. 1 or the pharmaceutically acceptable salt thereof is administered three or more times weekly.

In some embodiments, Compound No. 1 or the pharmaceutically acceptable salt thereof is administered with one or more drug holidays.

In some embodiments, Compound No. 1 or the pharmaceutically acceptable salt thereof is administered without any drug holiday.

In some embodiments, Compound No. 1 or the pharmaceutically acceptable salt thereof is administered at a dosage (e.g., a weekly dosage) of about 60 mg, about 80 mg, about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, Compound No. 1 or the pharmaceutically acceptable salt thereof is administered at a dosage (e.g., a weekly dosage) of about 80 mg, about 160 mg, about 180 mg, about 240 mg, about 320 mg, or about 400 mg.

In some embodiments. Compound No. 1 or the pharmaceutically acceptable salt thereof is administered at a dosage (e.g., a weekly dosage) of about 80±40 mg, about 80±30 mg, about 80±20 mg, about 80±10 mg, about 80±5 mg, about 80±4 mg, about 80±3 mg, about 80±2 mg, or about 80±1 mg (e.g., about 80 mg).

In some embodiments, Compound No. 1 or the pharmaceutically acceptable salt thereof is administered at a dosage (e.g., a weekly dosage) of about 160±60 mg, about 160±50 mg, about 160±40 mg, about 160±30 mg, about 160±20 mg, about 160±10 mg, about 160±5 mg, about 160±4 mg, about 160±3 mg, about 160±2 mg, or about 160±1 mg (e.g., about 160 mg).

In some embodiments, Compound No. 1 or the pharmaceutically acceptable salt thereof is administered at a dosage (e.g., a weekly dosage) of about 180±60 mg, about 180±50 mg, about 180±40 mg, about 180±30 mg, about 180±20 mg, about 180±10 mg, about 180±5 mg, about 180±4 mg, about 180±3 mg, about 180±2 mg, or about 180±1 mg (e.g., about 180 mg).

In some embodiments, Compound No. 1 or the pharmaceutically acceptable salt thereof is administered at a dosage (e.g., a weekly dosage) of about 240±60 mg, about 240±50 mg, about 240±40 mg, about 240±30 mg, about 240±20 mg, about 240±10 mg, about 240±5 mg, about 240±4 mg, about 240±3 mg, about 240±2 mg, or about 240±1 mg (e.g., about 240 mg).

In some embodiments, Compound No. 1 or the pharmaceutically acceptable salt thereof is administered at a dosage (e.g., a weekly dosage) of about 320±60 mg, about 320±50 mg, about 320±40 mg, about 320±30 mg, about 320±20 mg, about 320±10 mg, about 320=5 mg, about 320±4 mg, about 320±3 mg, about 320±2 mg, or about 32±1 mg (e.g., about 320 mg).

In some embodiments, Compound No. 1 or the pharmaceutically acceptable salt thereof is administered at a dosage (e.g., a weekly dosage) of about 400±60 mg, about 400±50 mg, about 400±40 mg, about 400±30 mg, about 400±20 mg, about 400±10 mg, about 400±5 mg, about 400±4 mg, about 400±3 mg, about 400±0.2 mg, or about 400±1 mg (e.g., about 400 mg).

In some embodiments, Compound No. 1 or the pharmaceutically acceptable salt thereof is intravenously administered for about 10 minutes weekly, about 20 minutes weekly, about 30 minutes weekly, about 40 minutes weekly, about 50 minutes weekly, about 60 minutes weekly, about 70 minutes weekly, about 80 minutes weekly, about 90 minutes weekly, about 100 minutes weekly, about 110 minutes weekly, or about 120 minutes weekly.

In some embodiments, Compound No. 1 or the pharmaceutically acceptable salt thereof is administered for about 1 day or longer, about 2 days or longer, about 3 days or longer, about 4 days or longer, about 5 days or longer, about 6 days or longer, about 7 days or longer, about 14 days or longer, about 21 days or longer, about 42 days or longer, about 63 days or longer, about 84 days or longer, about 105 days or longer, about 126 days or longer, about 147 days or longer, about 168 days or longer, about 189 days or longer, or about 210 days or longer.

In some embodiments, Compound No. 1 or the pharmaceutically acceptable salt thereof is administered for about 1 day, about 2 days, about 3 days, about 4 days, about 5 days, about 6 days, about 7 days, about 14 days, about 21 days, about 42 days, about 63 days, about 84 days, about 105 days, about 126 days, about 147 days, about 168 days, about 189 days, or about 210 days.

In some embodiments, Compound No. 1 or the pharmaceutically acceptable salt thereof is administered for about 21 days.

In some embodiments, Compound No. 1 or the pharmaceutically acceptable salt thereof is administered once, twice, or three times in about every 21 days.

In some embodiments, Compound No. 1 or the pharmaceutically acceptable salt thereof is administered three times in about every 21 days.

In some embodiments, Compound No. 1 or the pharmaceutically acceptable salt thereof is administered once weekly for about 21 days.

In some embodiments, Compound No. 1 or the pharmaceutically acceptable salt thereof is administered at day 1 in about every 21 days.

In some embodiments, Compound No. 1 or the pharmaceutically acceptable salt thereof is administered at day 8 in about every 21 days.

In some embodiments, Compound No. 1 or the pharmaceutically acceptable salt thereof is administered at day 15 in about every 21 days.

In some embodiments, Compound No. 1 or the pharmaceutically acceptable salt thereof is administered at day 1, day 8, and day 15 in about every 21 days.

In some embodiments, Compound No. 1 or the pharmaceutically acceptable salt thereof is intravenously administered for about 30 minutes weekly.

In some embodiments, Compound No. 1 or the pharmaceutically acceptable salt thereof is intravenously administered for about 30 minutes weekly for about 21 days.

In some embodiments, Compound No. 1 or the pharmaceutically acceptable salt thereof is intravenously administered for about 30 minutes at day 1 in about every 21 days.

In some embodiments, Compound No. 1 or the pharmaceutically acceptable salt thereof is intravenously administered for about 30 minutes at day 8 in about every 21 days.

In some embodiments, Compound No. 1 or the pharmaceutically acceptable salt thereof is intravenously administered for about 30 minutes at day 15 in about every 21 days.

In some embodiments, Compound No. 1 or the pharmaceutically acceptable salt thereof is intravenously administered for about 30 minutes at day 1, day 8, and day 15 in about every 21 days.

In some embodiments, Compound No. 1 or the pharmaceutically acceptable salt thereof is administered for about 1 day or longer, about 2 days or longer, about 3 days or longer, about 4 days or longer, about 5 days or longer, about 6 days or longer, about 7 days or longer, about 14 days or longer, about 21 days or longer, about 28 days or longer, about, 56 days or longer, about 84 days or longer, about 112 days or longer, about 140 days or longer, about 168 days or longer, about 196 days or longer, about 224 days or longer, about 252 days or longer, or about 280 days or longer.

In some embodiments, Compound No. 1 or the pharmaceutically acceptable salt thereof is administered for about 1 day, about 2 days, about 3 days, about 4 days, about 5 days, about 6 days, about 7 days, about 14 days, about 21 days, about 28 days, about, 56 days, about 84 days, about 112 days, about 140 days, about 168 days, about 196 days, about 224 days, about 252 days, or about 280 days.

In some embodiments, Compound No. 1 or the pharmaceutically acceptable salt thereof is administered once, twice, three times, or four times in about every 28 days.

In some embodiments, Compound No. 1 or the pharmaceutically acceptable salt thereof is administered three times in about every 28 days.

In some embodiments, Compound No. 1 or the pharmaceutically acceptable salt thereof is administered four times in about every 28 days.

In some embodiments, Compound No. 1 or the pharmaceutically acceptable salt thereof is administered four times in about the first 28 days, and is administered three times in about every 28 days thereafter.

In some embodiments, Compound No. 1 or the pharmaceutically acceptable salt thereof is administered once weekly in about every 28 days.

In some embodiments, Compound No. 1 or the pharmaceutically acceptable salt thereof is administered once weekly for the first three weeks in about every 28 days.

In some embodiments, Compound No. 1 or the pharmaceutically acceptable salt thereof is administered once weekly in about the first 28 days, and is administered once weekly for the first three weeks in about every 28 days thereafter.

In some embodiments, Compound No. 1 or the pharmaceutically acceptable salt thereof is intravenously administered for about 30 minutes weekly in about every 28 days.

In some embodiments, Compound No. 1 or the pharmaceutically acceptable salt thereof is intravenously administered for about 30 minutes weekly for the first three weeks in about every, 28 days.

In some embodiments, Compound No. 1 or the pharmaceutically acceptable salt thereof is intravenously administered for about 30 minutes weekly in about the first 28 days, and is intravenously administered for about 30 minutes weekly for the first three weeks in about every 28 days thereafter.

Administrations of Paclitaxel

In some embodiments, the at least one additional therapeutic agent (e.g., paclitaxel or a pharmaceutically acceptable salt thereof) is administered by eternal administration.

In some embodiments, the at least one additional therapeutic agent (e.g., paclitaxel or a pharmaceutically acceptable salt thereof) is administered by oral administration.

In some embodiments, the at least one additional therapeutic agent (e.g., paclitaxel or a pharmaceutically acceptable salt thereof) is administered by parenteral administration.

In some embodiments, the at least one additional therapeutic agent (e.g., paclitaxel or a pharmaceutically acceptable salt thereof) is administered by intravenous administration.

In some embodiments, the at least one additional therapeutic agent (e.g., paclitaxel or a pharmaceutically acceptable salt thereof) is administered once weekly.

In some embodiments, the at least one additional therapeutic agent (e.g., paclitaxel or a pharmaceutically acceptable salt thereof) is administered twice weekly.

In some embodiments, the at least one additional therapeutic agent (e.g., paclitaxel or a pharmaceutically acceptable salt thereof) is administered three or more times weekly.

In some embodiments, the at least one additional therapeutic agent (e.g., paclitaxel or a pharmaceutically acceptable salt thereof) is administered for about 1 day or longer, about 2 days or longer, about 3 days or longer, about 4 days or longer, about 5 days or longer, about 6 days or longer, about 7 days or longer, about 14 days or longer, about 21 days or longer, about 42 days or longer, about 63 days or longer, about 84 days or longer, about 105 days or longer, about 126 days or longer, about 147 days or longer, about 168 days or longer, about 189 days or longer, or about 210 days or longer.

In some embodiments, the at least one additional therapeutic agent (e.g., paclitaxel or a pharmaceutically acceptable salt thereof) is administered for about 1 day, about 2 days, about 3 days, about 4 days, about 5 days, about 6 days, about 7 days, about 14 days, about 21 days, about 42 days, about 63 days, about 84 days, about 105 days, about 126 days, about 147 days, about 168 days, about 189 days, or about 210 days.

In some embodiments, the at least one additional therapeutic agent (e.g., paclitaxel or a pharmaceutically acceptable salt thereof) is administered with one or more drug holidays.

In some embodiments, the at least one additional therapeutic agent (e.g., paclitaxel or a pharmaceutically acceptable salt thereof) is administered without any drug holiday.

In some embodiments, the at least one additional therapeutic agent (e.g., paclitaxel or a S0 pharmaceutically acceptable salt thereof) is administered for about 21 days.

In some embodiments, the at least one additional therapeutic agent (e.g., paclitaxel or a pharmaceutically acceptable salt thereof) is administered once, twice, or three times in about every 21 days.

In some embodiments, the at least one additional therapeutic agent (e.g., paclitaxel or a pharmaceutically acceptable salt thereof) is administered three times in about every 21 days.

In some embodiments, the at least one additional therapeutic agent (e.g., paclitaxel or a pharmaceutically acceptable salt thereof) is administered once weekly for about 21 days.

In some embodiments, the at least one additional therapeutic agent (e.g., paclitaxel or a pharmaceutically acceptable salt thereof) is administered daily.

In some embodiments, the at least one additional therapeutic agent (e.g., paclitaxel or a pharmaceutically acceptable salt thereof) is administered daily for about 21 days.

In some embodiments, the at least one additional therapeutic agent (e.g., paclitaxel or a pharmaceutically acceptable salt thereof) is administered once daily for about 21 days.

In some embodiments, the at least one additional therapeutic agent (e.g., paclitaxel or a pharmaceutically acceptable salt thereof) is administered two or more times daily for about 21 days.

In some embodiments, the at least one additional therapeutic agent (e.g., paclitaxel or a pharmaceutically acceptable salt thereof) is administered at day 1 in about every 21 days.

In some embodiments, the at least one additional therapeutic agent (e.g., paclitaxel or a pharmaceutically acceptable salt thereof) is administered at day 8 in about every 21 days.

In some embodiments, the at least one additional therapeutic agent (e.g., paclitaxel or a pharmaceutically acceptable salt thereof) is administered at day 21 in about every 21 days.

In some embodiments, the at least one additional therapeutic agent (e.g., paclitaxel or a pharmaceutically acceptable salt thereof) is administered at day 1, day 8, and day 21 in about every 21 days.

In some embodiments, the at least one additional therapeutic agent (e.g., paclitaxel or a pharmaceutically acceptable salt thereof) is administered at a dosage (e.g., a weekly dosage) of about 60 $mg/m^2$, about 80 $mg/m^2$ about 100 $mg/m^2$, about 120 $mg/m^2$, about 140 $mg/m^2$, about 160 $mg/m^2$, about 180 $mg/m^2$, about 200 $mg/m^2$, about 220 $mg/m^2$, about 240 $mg/m^2$, about 260 $mg/m^2$ about 280 $mg/m^2$, about 300 $mg/m^2$ about 320 $mg/m^2$, about 340 $mg/m^2$ about 360 $mg/m^2$ about 380 $mg/m^2$ about 400 $mg/m^2$ about 420 $mg/m^2$, about 440 $mg/m^2$ about 460 $nm/m^2$, about 480 $mg/m^2$, or about 500 $mg/m^2$.

In some embodiments, the at least one additional therapeutic agent (e.g., paclitaxel or a pharmaceutically acceptable salt thereof) is administered at a dosage (e.g., a weekly dosage) of about 80±40 $mg/m^2$, about 80±30 $mg/m^2$ about 80±20 $mg/m^2$, about 80±10 $mg/m^2$, about 80±5 $mg/m^2$ about 80±4 $mg/m^2$, about 80±3 $mg/m^2$, about 80±2 $mg/m^2$ or about 80±1 $mg/m^2$ (e.g., about 80 mg/m).

Administrations of Osimertinib

In some embodiments, the at least one additional therapeutic agent (e.g., osimertinib or a pharmaceutically acceptable salt thereof) is administered by enteral administration.

In some embodiments, the at least one additional therapeutic agent (e.g., osimertinib or a pharmaceutically acceptable salt thereof) is administered by oral administration.

In some embodiments, the at least one additional therapeutic agent (e.g., osimertinib or a pharmaceutically acceptable salt thereof) is administered by parenteral administration.

In some embodiments, the as least one additional therapeutic agent (e.g., osimertinib or a pharmaceutically acceptable salt thereof) is administered by intravenous administration.

In some embodiments, the at least one additional therapeutic agent (e.g., osimertinib or a pharmaceutically acceptable salt thereof) is administered once weekly.

In some embodiments, the at least one additional therapeutic agent (e.g., osimertinib or a pharmaceutically acceptable salt thereof) is administered twice weekly.

In some embodiments, the at least one additional therapeutic agent (e.g., osimertinib or a pharmaceutically acceptable salt thereof) is administered three or more times weekly.

In some embodiments, the at least one additional therapeutic agent (e.g., osimertinib or a pharmaceutically acceptable salt thereof) is administered for about 1 day or longer, about 2 days or longer, about 3 days or longer, about 4 days or longer, about 5 days or longer, about 6 days or longer, about 7 days or longer, about 14 days or longer, about 21 days or longer, about 42 days or longer, about 63 days or longer, about 84 days or longer, about 105 days or longer, about 126 days or longer, about 147 days or longer, about 168 days or longer, about 189 days or longer, or about 210 days or longer.

In some embodiments, the at least one additional therapeutic agent (e.g., osimertinib or a pharmaceutically acceptable salt thereof) is administered for about 1 day, about 2 days, about 3 days, about 4 days, about 5 days, about 6 days, about 7 days, about 14 days, about 21 days, about 42 days, about 63 days, about 84 days, about 105 days, about 126 days, about 147 days, about 168 days, about 189 days, or about 210 days.

In some embodiments, the at least one additional therapeutic agent (e.g., osimertinib or a pharmaceutically acceptable salt thereof) is administered with one or more drug holidays.

In some embodiments, the at least one additional therapeutic agent (e.g., osimertinib or a pharmaceutically acceptable salt thereof) is administered without any drug holiday.

In some embodiments, the at least one additional therapeutic agent (e.g., osimertinib or a pharmaceutically acceptable salt thereof) is administered for about 21 days.

In some embodiments, the at least one additional therapeutic agent (e.g., osimertinib or a pharmaceutically acceptable salt thereof) is administered once, twice, or three times in about every 21 days.

In some embodiments, the at least one additional therapeutic agent (e.g., osimertinib or a pharmaceutically acceptable salt thereof) is administered three times in about every 21 days.

In some embodiments, the at least one additional therapeutic agent (e.g., osimertinib or a pharmaceutically acceptable salt thereof) is administered once weekly for about 21 days.

In some embodiments, the at least one additional therapeutic agent (e.g., osimertinib or a pharmaceutically acceptable salt thereof) is administered daily.

In some embodiments, the at least one additional therapeutic agent (e.g., osimertinib or a pharmaceutically acceptable salt thereof) is administered daily for about 21 days.

In some embodiments, the at least one additional therapeutic agent (e.g., osimertinib or a pharmaceutically acceptable salt thereof) is administered once daily for about 21 days.

In some embodiments, the at least one additional therapeutic agent (e.g., osimertinib or a pharmaceutically acceptable salt thereof) is administered two or more times daily for about 21 days.

In some embodiments, an oral formulation of the at least one additional therapeutic agent (e.g., osimertinib or a pharmaceutically acceptable salt thereof) is administered.

In some embodiments, a tablet of the at least one additional therapeutic agent (e.g., osimertinib or a pharmaceutically acceptable salt thereof) is administered.

In some embodiments, a tablet of a mesylate salt of osimertinib is administered.

In some embodiments, the at least one additional therapeutic agent (e.g., osimertinib or a pharmaceutically acceptable salt thereof) is administered once daily for about 21 days.

In some embodiments, the at least one additional therapeutic agent (e.g., osimertinib or a pharmaceutically acceptable salt thereof) is administered at a dosage (e.g., a daily dosage) of about 60 mg, about 80 mg, about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the at least one additional therapeutic agent (e.g., osimertinib or a pharmaceutically acceptable salt thereof) is administered at a dosage (e.g., a daily dosage) of about 80 mg, about 160 mg, or about 240 mg.

In some embodiments, the at least one additional therapeutic agent (e.g., osimertinib or a pharmaceutically acceptable salt thereof) is administered at a dosage (e.g., a daily dosage) of about 80±40 mg, about 80±30 mg, about 80±20 mg, about 80±10 mg, about 80±5 mg, about 80±4 mg, about 80±3 mg, about 80±2 mg, or about 80±1 mg (e.g., about 80 mg).

Administration of Ruxolitinib

In some embodiments, the at least one additional therapeutic agent (e.g., ruxolitinib or a pharmaceutically acceptable salt thereof) is administered by enternal administration.

In some embodiments, the at least one additional therapeutic agent (e.g., ruxolitinib or a pharmaceutically acceptable salt thereof) is administered by oral administration.

In some embodiments, the at least one additional therapeutic agent (e.g., ruxolitinib or a pharmaceutically acceptable salt thereof) is administered once weekly.

In some embodiments, the at least one additional therapeutic agent (e.g., ruxolitinib or a pharmaceutically acceptable salt thereof) is administered twice weekly.

In some embodiments, the at least one additional therapeutic agent (e.g., ruxolitinib or a pharmaceutically acceptable salt thereof) is administered three or more times weekly.

In some embodiments, the at least one additional therapeutic agent (e.g., ruxolitinib or a pharmaceutically acceptable salt thereof) is administered for about 1 day or longer, about 2 days or longer, about 3 days or longer, about 4 days or longer, about 5 days or longer, about 6 days or longer about 7 days or longer, about 14 days or longer, about 21 days or longer, about 42 days or longer, about 63 days or longer, about 84 days or longer, about 105 days or longer, about 126 days or longer, about 147 days or longer, about 168 days or longer, about 189 days or longer, or about 210 days or longer.

In some embodiments, the at least one additional therapeutic agent (e.g., ruxolitinib or a pharmaceutically acceptable salt thereof) is administered for about 1 day, about 2 days, about 3 days, about 4 days, about 5 days, about 6 days, about 7 days, about 14 days, about 21 days, about 42 days, about 63 days, about 84 days, about 105 days, about 126 days, about 147 days, about 168 days, about 189 days, or about 210 days.

In some embodiments, the at least one additional therapeutic agent (e.g., ruxolitinib or a pharmaceutically acceptable salt thereof) is administered with one or more drug holidays.

In some embodiments, the at least one additional therapeutic agent (e.g., ruxolitinib or a pharmaceutically acceptable salt thereof) is administered without any drug holiday.

In some embodiments, the at least one additional therapeutic agent (e.g., ruxolitinib or a pharmaceutically acceptable salt thereof) is administered daily.

In some embodiments, the at least one additional therapeutic agent (e.g., ruxolitinib or a pharmaceutically acceptable salt thereof is administered once, twice, or three or more times daily.

In some embodiments, the at least one additional therapeutic agent (e.g., ruxolitinib or a pharmaceutically acceptable salt thereof) is administered twice daily.

In some embodiments, the at least one additional therapeutic agent (e.g., ruxolitinib or a pharmaceutically acceptable salt thereof) is administered twice daily for about 28 days.

In some embodiments, the at least one additional therapeutic agent (e.g., ruxolitinib or a pharmaceutically acceptable salt thereof) is not administered in about the first 28 days, and is administered daily thereafter.

In some embodiments, the at least one additional therapeutic agent (e.g., ruxolitinib or a pharmaceutically acceptable salt thereof) is not administered in about the first 28 days, and is administered twice daily thereafter.

In some embodiments, an oral formulation of the at least one additional therapeutic agent (e.g., ruxolitinib or a pharmaceutically acceptable salt thereof) is administered.

In some embodiments, a tablet of the at least one additional therapeutic agent (e.g., ruxolitinib or a pharmaceutically acceptable salt thereof) is administered. In some embodiments, the tablet comprises about 5 mg, about 10 mg, about 15 mg, about 20 mg, or about 25 mg of ruxolitinib or a pharmaceutically acceptable salt thereof.

In some embodiments, the at least one additional therapeutic agent (e.g., ruxolitinib or a pharmaceutically acceptable salt thereof) is administered at a dosage (e.g., a daily dosage) of about 10 mg, about 20 µmg, about 30 mg, about 40 mg, or about 50 mg.

In some embodiments, the at least one additional therapeutic agent (e.g., ruxolitinib or a pharmaceutically acceptable salt thereof) is administered at a dosage (e.g., a daily dosage) of about 10±5 mg, about 10±4 mg, about 10±3 mg, about 10±2 mg, about 10±1 (e.g., about 10 mg).

In some embodiments, the at least one additional therapeutic agent (e.g., ruxolitinib or a pharmaceutically acceptable salt thereof is administered at a dosage (e.g., a daily dosage) of about 20±10 mg, about 20±8 mg, about 20±6 mg, about 20±5 mu, about 20±4 mg, about 20±3 mg, about 20±2 trig, about 20±1 (e.g., about 20 mg).

In some embodiments, the at least one additional therapeutic agent (e.g., ruxolitinib or a pharmaceutically acceptable salt thereof) is administered at a dosage (e.g., a daily dosage) of about 30±15 mg, about 30±10 mg, about 30±8 trig, about 30±6 mg, about 30±5 mg, about 30±4 mg, about 30±3 mg, about 30±2 mg, about 30±1 (e.g., about 30 mg).

In some embodiments, the at least one additional therapeutic agent (e.g., ruxolitinib or a pharmaceutically acceptable salt thereof) is administered at a dosage (e.g., a daily dosage) of about 40±20 mg, about 40±15 mg, about 40±10 mg, about 40±8 mg, about 40±6 mg, about 40±5 mg, about 40±4 mg, about 40±3 mg, about 40±2 mg, about 40±1 (e.g., about 40 ma).

In some embodiments, the at least one additional therapeutic agent (e.g., ruxolitinib or a pharmaceutically acceptable salt thereof) is administered at a dosage (e.g., a daily dosage) of about 50±25 mg, about 50±20 mg, about 50±15 mg, about 50±10 mg, about 50±8 mg, about 50±6 mg, about 50±5 mg, about 50±4 mg, about 50±3 mg, about 50±2 mg, about 50±1 (e.g., about 50 mg).

In some embodiments, the subject has a platelet count ranging from about $50\times10^9$/L to about $100\times10^9$/L.

In some embodiments, the subject has a platelet count ranging from about $50\times10^9$/L to about $100\times10^9$/L, and the at least one additional therapeutic agent (e.g., ruxolitinib or a pharmaceutically acceptable salt thereof) is administered at a dosage (e.g., a daily dosage) of about 10±5 mg, about 10±4 mg, about 10±3 mg, about 10±2 mg, about 10±1 (e.g., about 10 mg).

In some embodiments, the subject has a platelet count ranging from about $50\times10^9$/L to about $100\times10^9$/L, and a tablet comprising about 5 mg of the at least one additional therapeutic agent (e.g., ruxolitinib or a pharmaceutically acceptable salt thereof) is administered twice daily.

In some embodiments, the subject has a platelet count ranging from about $100\times10^9$/L to about $200\times10^9$/L.

In some embodiments, the subject has a platelet count ranging from about $100\times10^9$/L to about $200\times10^9$/L, and the at least one additional therapeutic agent (e.g., ruxolitinib or a pharmaceutically acceptable salt thereof) is administered at a dosage (e.g., a daily dosage) of about 30±15 mg, about 30±10 mg, about 30±8 mg, about 30±6 mg, about 30±5 mg, about 30±4 mg, about 30±3 mg, about 30±2 mg, about 30±1 (e.g., about 30 mg).

In some embodiments, the subject has a platelet count ranging from about $100\times10^9$/L to about $200\times10^9$/L, and a tablet comprising about 15 mg of the at least one additional therapeutic agent (e.g., ruxolitinib or a pharmaceutically acceptable salt thereof) is administered twice daily.

In some embodiments, the subject has a platelet count greater than about $200\times10^9$/L.

In some embodiments, the subject has a platelet count greater than about $200\times10^9$/L, and the at least one additional therapeutic agent (e.g., ruxolitinib or a pharmaceutically acceptable salt thereof) is administered at a dosage (e.g., a daily dosage) of about 40±20 mg, about 40±15 mg, about 40±10 mg, about 40±8 mg, about 40±6 mg, about 40±5 mg, about 40±4 mg, about 40±0.3 mg, about 40±2 mg, about 40±1 (e.g., about 40 mg).

In some embodiments, the subject has a platelet count greater than about $200\times10^9$/L, and a tablet comprising about 20 mg of the at least one additional therapeutic agent (e.g., ruxolitinib or a pharmaceutically acceptable salt thereof) is administered twice daily.

Administrations of Compound No. A

In some embodiments, the at least one additional therapeutic agent (e.g., Compound A or a pharmaceutically acceptable salt thereof) is administered by enteral administration.

In some embodiments, the at least one additional therapeutic agent (e.g., Compound A or a pharmaceutically acceptable salt thereof) is administered by oral administration.

In some embodiments, the at least one additional therapeutic agent (e.g., Compound A or a pharmaceutically acceptable salt thereof) is administered by parenteral administration.

In some embodiments, the at least one additional therapeutic agent (e.g., Compound A or a pharmaceutically acceptable salt thereof) is administered by intravenous administration.

In some embodiments, the at least one additional therapeutic agent (e.g., Compound A or a pharmaceutically acceptable salt thereof) is intravenously administered for about 10 minutes weekly, about 20 minutes weekly, about 30 minutes weekly, about 40 minutes weekly, about 50 minutes weekly, about 60 minutes weekly, about 70 minutes weekly, about 80 minutes weekly, about 90 minutes weekly, about 100 minutes weekly, about 110 minutes weekly, or about 120 minutes weekly.

In some embodiments, the at least one additional therapeutic agent (e.g., Compound A or a pharmaceutically acceptable salt thereof) is administered for about 1 day or longer, about 2 days or longer, about 3 days or longer, about 4 days or longer, about 5 days or longer, about 6 days or longer, about 7 days or longer, about 14 days or longer, about 21 days or longer, about 28 days or longer, about, 56 days or longer, about 84 days or longer, about 112 days or longer, about 140 days or longer, about 168 days or longer, about 196 days or longer, about 224 days or longer, about 252 days or longer, or about 280 days or longer.

In some embodiments, the at least one additional therapeutic agent (e.g., Compound A or a pharmaceutically acceptable salt thereof) is administered for about 1 day, about 2 days, about 3 days, about 4 days, about 5 days, about 6 days, about 7 days, about 14 days, about 21 days, about 28 days, about, 56 days, about 84 days, about 112 days, about 140 days, about 168 days, about 196 days, about 224 days, about 252 days, or about 280 days.

In some embodiments, the at least one additional therapeutic agent (e.g., Compound A or a pharmaceutically acceptable salt thereof) is administered once, twice, three times, or four times in about every 28 days.

In some embodiments, the al least one additional therapeutic agent (e.g., Compound A or a pharmaceutically acceptable salt thereof) is administered three times in about every 28 days.

In some embodiments, the at least one additional therapeutic agent (e.g., Compound A or a pharmaceutically acceptable salt thereof) is administered four times in about every 28 days.

In some embodiments, the at least one additional therapeutic agent (e.g., Compound A or a pharmaceutically acceptable salt thereof) is administered four times in about the first 28 days, and is administered three times in about every 28 days thereafter.

In some embodiments, the at least one additional therapeutic agent (e.g., Compound A or a pharmaceutically acceptable salt thereof) is administered once weekly in about every 28 days.

In some embodiments, the at least one additional therapeutic agent (e.g., Compound A or a pharmaceutically acceptable salt thereof) is administered once weekly for the first three weeks in about every 28 days.

In some embodiments, the at least one additional therapeutic agent (e.g., Compound A or a pharmaceutically acceptable salt thereof) is administered once weekly in about the first 28 days, and is administered once weekly for the first three weeks in about every 28 days thereafter.

In some embodiments, the at least one additional therapeutic agent (e.g., Compound A or a pharmaceutically acceptable salt thereof) is intravenously administered for about 30 minutes weekly in about every 28 days.

In some embodiments, the at least one additional therapeutic agent (e.g., Compound A or a pharmaceutically acceptable salt thereof) is intravenously administered for about 30 minutes weekly for the first three weeks in about every 28 days.

In some embodiments, the at least one additional therapeutic agent (e.g., Compound A or a pharmaceutically acceptable salt thereof) is administered for about 30 minutes weekly in about the first 28 days, and is administered for about 30 minutes weekly for the first three weeks in about every 28 days thereafter.

In some embodiments, the at least one additional therapeutic agent (e.g., Compound A or a pharmaceutically acceptable salt thereof) is administered at a dosage (e.g., a weekly dosage) of about 45 mg or less.

In some embodiments, the at least one additional therapeutic agent (e.g., Compound A or a pharmaceutically acceptable salt thereof) is administered at a dosage (e.g., a weekly dosage) of about 5 mg, about 10 mg, about 15 mg, about 20 mg, about 25 mg, about 30 mg, about 35 mg, about 40 me, or about 45 mg.

In some embodiments, the at least one additional therapeutic agent (e.g., Compound A or a pharmaceutically acceptable salt thereof) is administered at a dosage (e.g., a weekly dosage) of about 30 mg or about 45 mg.

In some embodiments, the at least one additional therapeutic agent (e.g., Compound A or a pharmaceutically acceptable salt thereof) is administered at a dosage (e.g., a weekly dosage) of about 30±20 mg, about 30±10 mg, about 30±5 mg, about 30±4 mg, about 30±3 mg, about 30±2 mg, or about 30±1 mg (e.g., about 30 mg).

In some embodiments, the at least one additional therapeutic agent (e.g., Compound A or a pharmaceutically acceptable salt thereof) is administered at a dosage (e.g., a weekly dosage) of about 45±20 mg, about 45±10 mg, about 45±5 mg, about 45±4 mg, about 45±3 mg, about 45±2 mg, or about 45±1 mg (e.g., about 45 mg).

Relationships Between Administrations

In some embodiments, Compound. No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered simultaneously.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered in a co-formulation.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered in separate formulations.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered sequentially or in alternation.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered sequentially.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered in temporal proximity.

In some embodiments, Compound No. 1 or the pharmaceutically acceptable salt thereof is administered prior to the administration of the at least one additional therapeutic agent (e.g., paclitaxel, osimertinib, ruxolitinib. Compound A, or a pharmaceutically acceptable salt thereof).

In some embodiments, Compound No. 1 or the pharmaceutically acceptable salt thereof is administered at about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, or about 12 hours prior to the administration of the at least one additional therapeutic agent (e.g., paclitaxel, osimertinib, ruxolitinib. Compound A, or a pharmaceutically acceptable salt thereof).

In some embodiments, the at least one additional therapeutic agent (e.g., paclitaxel, osimertinib, ruxolitinib, Compound A, or a pharmaceutically acceptable salt thereof) is administered at about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, or about 12 hours prior to the administration of Compound No. 1 or the pharmaceutically acceptable salt thereof.

In some embodiments, the at least one additional therapeutic agent (e.g., paclitaxel, osimertinib, ruxolitinib, Compound A, or a pharmaceutically acceptable salt thereof) is administered prior to the administration of Compound No. 1 or the pharmaceutically acceptable salt thereof.

In some embodiments, Compound No. 1 or the pharmaceutically acceptable salt thereof and the at least one additional therapeutic agent (e.g., paclitaxel, osimertinib, ruxolitinib, Compound A. or a pharmaceutically acceptable salt thereof) are administered in alternation.

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered by a same route of administration (e.g., parenteral administration (e.g., intravenous administration)).

In some embodiments, Compound No. 1 or the pharmaceutically acceptable salt thereof and the at least one additional therapeutic agent (e.g., paclitaxel, osimertinib, ruxolitinib, Compound A, or a pharmaceutically acceptable salt thereof) are administered by different routes of administration.

In some embodiments, at least two additional therapeutic agents (e.g., ruxolitinib or a pharmaceutically acceptable salt thereof, and Compound A or a pharmaceutically acceptable salt thereof) are administered.

In some embodiments, the at least two additional therapeutic agents (e.g., ruxolitinib or a pharmaceutically acceptable salt thereof, and Compound A or a pharmaceutically acceptable salt thereof) are administered simultaneously.

In some embodiments, the at least two additional therapeutic agents (e.g., ruxolitinib or a pharmaceutically acceptable salt thereof, and Compound A or a pharmaceutically acceptable salt thereof) are administered in a co-formulation.

In some embodiments, the at least two additional therapeutic agents (e.g., ruxolitinib or a pharmaceutically acceptable salt thereof, and Compound A or a pharmaceutically acceptable salt thereof) are administered in separate formulations.

In some embodiments, the at least two additional therapeutic agents (e.g., ruxolitinib or a pharmaceutically acceptable salt thereof, and Compound A or a pharmaceutically acceptable salt thereof) are administered sequentially or in alternation.

In some embodiments, the at least two additional therapeutic agents (e.g., ruxolitinib or a pharmaceutically acceptable salt thereof, and Compound A or a pharmaceutically acceptable salt thereof) are administered sequentially.

In some embodiments, the at least two additional therapeutic agents (e.g., ruxolitinib or a pharmaceutically acceptable salt thereof, and Compound A or a pharmaceutically acceptable salt thereof) are administered in temporal proximity.

In some embodiments, the at least two additional therapeutic agents (e.g., ruxolitinib or a pharmaceutically acceptable salt thereof, and Compound A or a pharmaceutically acceptable salt thereof) are administered in alternation.

In some embodiments, the at least two additional therapeutic agents (e.g., ruxolitinib or a pharmaceutically acceptable salt thereof, and Compound A or a pharmaceutically acceptable salt thereof) are administered by a same route of administration.

In some embodiments, the at least two additional therapeutic agents (e.g., ruxolitinib or a pharmaceutically acceptable salt thereof, and Compound A or a pharmaceutically acceptable salt thereof) are administered by different routes of administration.

Exemplary Embodiments Related to Compound No. 1 and Paclitaxel

In some aspects, the present disclosure provides a combination comprising:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a method of treating or preventing cancer in a subject, comprising administering to the subject:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a method of treating or preventing relapsed and/or refractory SCLC in a subject, comprising administering to the subject:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a combination for treating or preventing cancer in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides a combination for treating or preventing relapsed and/or refractory SCLC in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides use of a combination in the manufacture of a medicament for treating or preventing cancer in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides use of a combination in the manufacture of a medicament for treating or preventing relapsed and/or refractory SCLC in a subject, wherein the combination comprises:

(i) a pharmaceutically effective amount of Compound No. 1 or a pharmaceutically acceptable salt thereof; and (ii) a pharmaceutically effective amount of paclitaxel or a pharmaceutically acceptable salt thereof.

In some aspects, the present disclosure provides Compound No. 1 or a pharmaceutically acceptable salt thereof for use in combination with paclitaxel or a pharmaceutically acceptable salt thereof in treating or preventing cancer in a subject.

In some aspects, the present disclosure provides Compound No. 1 or a pharmaceutically acceptable salt thereof for use in combination with paclitaxel or a pharmaceutically acceptable salt thereof in treating or preventing relapsed and/or refractory SCLC in a subject.

In some aspects, the present disclosure provides paclitaxel or a pharmaceutically acceptable salt thereof for use in combination with Compound No. 1 or a pharmaceutically acceptable salt thereof in treating or preventing cancer in a subject.

In some aspects, the present disclosure provides paclitaxel or a pharmaceutically acceptable salt thereof for use in combination with Compound No. 1 or a pharmaceutically acceptable salt thereof in treating or preventing relapsed and/or refractory SCLC in a subject.

In some embodiments, Compound No. 1 or the pharmaceutically acceptable salt thereof is administered at a dosage (e.g., a weekly dosage) of about 180 mg, about 240 mg, about 320 mg, or about 400 mg; and paclitaxel or the pharmaceutically acceptable salt thereof is administered at a dosage (e.g., a weekly dosage) of about 80 $mg/m^2$.

In some embodiments, Compound No. 1 or the pharmaceutically acceptable salt thereof is administered at day 1, day 8, and day 15 in about every 21 days; and paclitaxel or the pharmaceutically acceptable salt thereof is administered at day 1, day 8, and day 21 in about every 21 days.

Exemplary Embodiments Related to Compound No. 1 and Osimertinib

In some aspects, the present disclosure provides a combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides a method of treating or preventing cancer in a subject, comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a method of treating or preventing EGFR-TKI-resistant NSCLC in a subject, comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a combination for treating or preventing cancer in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides a combination for treating or preventing EGFR-TKI-resistant NSCLC in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides use of a combination in the manufacture of a medicament for treating or preventing cancer in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides use of a combination in the manufacture of a medicament for treating or preventing EGFR-TKI-resistant NSCLC in a subject, wherein the combination comprises:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides Compound No. 1 or a pharmaceutically acceptable salt thereof for use in combination with osimertinib or a pharmaceutically acceptable salt thereof in treating or preventing cancer in a subject.

In some aspects, the present disclosure provides Compound No. 1 or a pharmaceutically acceptable salt thereof for use in combination with osimertinib or a pharmaceutically acceptable salt thereof in treating or preventing EGFR-TKI-resistant WIC in a subject.

In some aspects, the present disclosure provides osimertinib or a pharmaceutically acceptable salt thereof for use in combination with Compound No. 1 or a pharmaceutically acceptable salt thereof in treating or preventing cancer in a subject.

In some aspects, the present disclosure provides osimertinib or a pharmaceutically acceptable salt thereof for use in combination with Compound No. 1 or a pharmaceutically acceptable salt thereof in treating or preventing EGFR-TKI-resistant NSCLC in a subject.

In some aspects, the present disclosure provides a method of treating or preventing cancer in a subject, wherein the cancer is resistant to treatment with osimertinib or a pharmaceutically acceptable salt thereof alone, the method comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a method of treating or preventing NSCLC in a subject, wherein the NSCLC is resistant to treatment with osimertinib or a pharmaceutically acceptable salt thereof alone, the method comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a combination for treating or preventing cancer in a subject, wherein the cancer is resistant to treatment with osimertinib or a pharmaceutically acceptable salt thereof alone, the combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides a combination for treating or preventing cancer in a subject, wherein the NSCLC is resistant to treatment with osimertinib or a pharmaceutically acceptable salt thereof alone, the combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides use of a combination in the manufacture of a medicament for treating or preventing cancer in a subject, wherein the cancer is resistant to treatment with osimertinib or a pharmaceutically acceptable salt thereof alone, the combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides use of a combination in the manufacture of a medicament for treating or preventing NSCLC in a subject, wherein the NSCLC is resistant to treatment with osimertinib or a pharmaceutically acceptable salt thereof alone, the combination comprising:

(i) a pharmaceutically effective amount of Compound No. 1 or a pharmaceutically acceptable salt thereof; and (ii) a pharmaceutically effective amount of osimertinib or a pharmaceutically acceptable salt thereof.

In some aspects, the present disclosure provides Compound No. 1 or a pharmaceutically acceptable salt thereof for use in combination with osimertinib or a pharmaceutically acceptable salt thereof in treating or preventing cancer in a subject, wherein the cancer is resistant to treatment with osimertinib or a pharmaceutically acceptable salt thereof alone.

In some aspects, the present disclosure provides Compound No. 1 or a pharmaceutically acceptable salt thereof for use in combination with osimertinib or a pharmaceutically acceptable salt thereof in treating or preventing EGFR-TKI-resistant NSCLC in a subject, wherein the NSCLC is resistant to treatment with osimertinib or a pharmaceutically acceptable salt thereof alone.

In some aspects, the present disclosure provides osimertinib or a pharmaceutically acceptable salt thereof for use in combination with Compound No. 1 or a pharmaceutically acceptable salt thereof in treating or preventing cancer in a subject, wherein the cancer is resistant to treatment with osimertinib or a pharmaceutically acceptable salt thereof alone.

In some aspects, the present disclosure provides osimertinib or a pharmaceutically acceptable salt thereof for use in combination with Compound No. 1 or a pharmaceutically acceptable salt thereof in treating or preventing EGFR-TKI-resistant NSCLC in a subject, wherein the NSCLC is resistant to treatment with osimertinib or a pharmaceutically acceptable salt thereof alone.

In some aspects, the present disclosure provides a method of treating or preventing cancer in a subject, wherein an EGFR mutation (e.g., G719X, S768I, L861Q, L747P, an exon 19 insertion, an exon 20 insertion, T790M, V843I, or any combination thereof) is identified in the subject (e.g., in a biological sample from the subject), comprising administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some aspects, the present disclosure provides a method of treating or preventing cancer in a subject, comprising:

(a) identifying the presence of an EGFR mutation (e.g., G719X, S768I, L861Q, L747P, an exon 19 insertion, an exon 20 insertion. T790M, V843I, or any combination thereof) in the subject (e.g., in a biological sample from the subject); and (b) administering to the subject:

(i) a pharmaceutically effective amount of Compound No. 1 or a pharmaceutically acceptable salt thereof; and (ii) a pharmaceutically effective amount of osimertinib or a pharmaceutically acceptable salt thereof (e.g., a mesylate salt of osimertinib).

In some embodiments, Compound No. 1 or the pharmaceutically acceptable salt thereof is administered at a dosage (e.g., a weekly dosage) of about 80 mg, about 160 mg, about 240 mg, about 320 mg, or about 400 mg; and osimertinib or a pharmaceutically acceptable salt thereof (e.g., a mesylate salt of osimertinib) is administered a dosage (e.g., a daily dosage) of about 80 mg.

In some embodiments, Compound No. 1 or the pharmaceutically acceptable salt thereof is administered at day 1, day 8, and day 15 in about every 21 days; and osimertinib or a pharmaceutically acceptable salt thereof (e.g., a mesylate salt of osimertinib) is administered in about every 21 days.

Exemplary Embodiments Related to Compound No. 1 and Ruxolitinib

In some aspects, the present disclosure provides a combination comprising:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a method of treating or preventing cancer in a subject, comprising administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a method of treating or preventing myelofibrosis in a subject, comprising administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a combination for treating or to preventing cancer in a subject, wherein the combination comprises:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a combination for treating or preventing myelofibrosis in a subject, wherein the combination comprises:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides use of a combination in the manufacture of a medicament for treating or preventing cancer in a subject, wherein the combination comprises:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides use of a combination in the manufacture of a medicament for treating or preventing myelofibrosis in a subject, wherein the combination comprises:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides Compound No. 1 or a pharmaceutically acceptable salt thereof for use in combination with ruxolitinib or a pharmaceutically acceptable salt thereof in treating or preventing cancer in a subject.

In some aspects, the present disclosure provides Compound No. 1 or a pharmaceutically acceptable salt thereof for use in combination with ruxolitinib or a pharmaceutically acceptable salt thereof in treating or preventing myelofibrosis in a subject.

In some aspects, the present disclosure provides ruxolitinib or a pharmaceutically acceptable salt thereof for use in combination with Compound No. 1 or a pharmaceutically acceptable salt thereof in treating or preventing cancer in a subject.

In some aspects, the present disclosure provides ruxolitinib or a pharmaceutically acceptable salt thereof for use in combination with Compound No. 1 or a pharmaceutically acceptable salt thereof in treating or preventing myelofibrosis in a subject.

In some aspects, the present disclosure provides a method of treating or preventing cancer in a subject, wherein the cancer resistant to treatment with a JAK inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a method of treating or preventing myelofibrosis in a subject, wherein the myelofibrosis is resistant to treatment with a JAK inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a combination for treating or preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a combination for treating or preventing myelofibrosis in a subject, wherein the myelofibrosis is resistant to treatment with a JAR inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides use of a combination in the manufacture of a medicament for treating or preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides use of a combination in the manufacture of a medicament for treating or preventing myelofibrosis in a subject, wherein the myelofibrosis is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides Compound No. 1 or a pharmaceutically acceptable salt thereof for use in combination with ruxolitinib or a pharmaceutically acceptable salt thereof in treating or preventing cancer in a subject, wherein the cancer is resistant to treatment with a JAK inhibitor (e.g., ruxolitinib or a pharmaceutically acceptable salt thereof) alone.

In some aspects, the present disclosure provides Compound No. 1 or a pharmaceutically acceptable salt thereof for use in combination with ruxolitinib or a pharmaceutically acceptable salt thereof in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides ruxolitinib or a pharmaceutically acceptable salt thereof for use in combination with Compound No. 1 or a pharmaceutically acceptable salt thereof in treating or preventing cancer in a subject, wherein the cancer is resistant to treatment with a JAK inhibitor (e.g., ruxolitinib or a pharmaceutically acceptable salt thereof alone.

In some aspects, the present disclosure provides ruxolitinib or a pharmaceutically acceptable salt thereof for use in combination with Compound No. 1 or a pharmaceutically acceptable salt thereof in treating or preventing myelofibrosis in a subject, wherein the myelofibrosis is resistant to treatment with a MK inhibitor (e.g., ruxolitinib or a pharmaceutically acceptable salt thereof) alone.

In some aspects, the present disclosure provides a method of treating or preventing cancer in a subject, wherein a JAK mutation (e.g., V617F) is identified in the subject (e.g., in a biological sample from the subject), comprising administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some aspects, the present disclosure provides a method of treating or preventing cancer in a subject, comprising:

(a) identifying the presence of a JAK mutation (e.g., V617F) in the subject (e.g., in a biological sample from the subject); and (b) administering to the subject:

(i) a pharmaceutically effective amount of Compound No. 1 or a pharmaceutically acceptable salt thereof; and (ii) a pharmaceutically effective amount of ruxolitinib or a pharmaceutically acceptable salt thereof.

In some embodiments, Compound No. 1 or the pharmaceutically acceptable salt thereof is administered at a dosage (e.g., a weekly dosage) of about 80 mg, about 160 mg, or about 240 mg.

In some embodiments, Compound No. 1 or the pharmaceutically acceptable salt thereof is administered once weekly in about the first 28 days, and is administered once weekly for the first three weeks in about every 28 days thereafter; and ruxolitinib or a pharmaceutically acceptable salt thereof is not administered in about the first 2l days, and is administered twice daily thereafter.

Exemplary Embodiments Related to Compound No. 1 and Compound A

In some aspects, the present disclosure provides a combination comprising:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a method of treating or preventing cancer in a subject, comprising administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a method of treating or preventing myelofibrosis in a subject, comprising administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a combination for treating or preventing cancer in a subject, wherein the combination comprises:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a combination for treating or preventing myelofibrosis in a subject, wherein the combination comprises:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides use of a combination in the manufacture of a medicament for treating or preventing cancer in a subject, wherein the combination comprises:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides use of a combination in the manufacture of a medicament for treating or preventing myelofibrosis in a subject, wherein the combination comprises:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides Compound No. 1 or a pharmaceutically acceptable salt thereof for use in combination with Compound A or a pharmaceutically acceptable salt thereof in treating or preventing cancer in a subject.

In some aspects, the present disclosure provides Compound No. 1 or a pharmaceutically acceptable salt thereof for use in combination with Compound A or a pharmaceutically acceptable salt thereof in treating or preventing myelofibrosis in a subject.

In some aspects, the present disclosure provides Compound A or a pharmaceutically acceptable salt thereof for use in combination with Compound No. 1 or a pharmaceutically acceptable salt thereof in treating or preventing cancer in a subject.

In some aspects, the present disclosure provides Compound A or a pharmaceutically acceptable salt thereof for use in combination with Compound No. 1 or a pharmaceutically acceptable salt thereof in treating or preventing myelofibrosis in a subject.

In some aspects, the present disclosure provides a method of treating or preventing cancer in a subject, wherein the cancer resistant to treatment with a JAI (inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a method of treating or preventing myelofibrosis in a subject, wherein the myelofibrosis is resistant to treatment with a JAK inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a combination for treating or to preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a combination for treating or preventing myelofibrosis in a subject, wherein the myelofibrosis is resistant to treatment with a JAR inhibitor (e.g., ruxolitinib or a pharmaceutically acceptable salt thereof) alone, the combination composing:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides use of a combination in the manufacture of a medicament for treating or preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides use of a combination in the manufacture of a medicament for treating or preventing myelofibrosis in a subject, wherein the myelofibrosis is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides Compound No. 1 or a pharmaceutically acceptable salt thereof for use in combination with Compound A or a pharmaceutically acceptable salt thereof in treating or preventing cancer in a subject, wherein the cancer is resistant to treatment with a JAK inhibitor (e.g., ruxolitinib or a pharmaceutically acceptable salt thereof) alone.

In some aspects, the present disclosure provides Compound No. 1 or a pharmaceutically acceptable salt thereof for use in combination with Compound A or a pharmaceutically acceptable salt thereof in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides Compound A or a pharmaceutically acceptable salt thereof for use in combination with Compound No. 1 or a pharmaceutically acceptable salt thereof in treating or preventing cancer in a subject, wherein the cancer is resistant to treatment with a JAK inhibitor (e.g., ruxolitinib or a pharmaceutically acceptable salt thereof alone.

In some aspects, the present disclosure provides Compound A or a pharmaceutically acceptable salt thereof for use in combination with Compound No. 1 or a pharmaceutically acceptable salt thereof in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides a method of treating or preventing cancer in a subject, wherein a JAK mutation (e.g., A/617F) is identified in the subject (e.g., in a biological sample from the subject), comprising administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some aspects, the present disclosure provides a method of treating or preventing cancer in a subject, comprising:

(a) identifying the presence of a mutation (e.g., V617F) in the subject (e.g., in a biological sample from the subject); and (b) administering to the subject:

(i) a pharmaceutically effective amount of Compound No. 1 or a pharmaceutically acceptable salt thereof; and (ii) a pharmaceutically effective amount of Compound A or a pharmaceutically acceptable salt thereof.

In some embodiments, Compound No. 1 or the pharmaceutically acceptable salt thereof is administered at a dosage (e.g., a weekly dosage) of about 80 mg, about 160 mg, or about 240 mg; and Compound A or the pharmaceutically acceptable salt thereof is administered at a dosage (e.g., a weekly dosage) of about 30 mg or about 45 mg.

In some embodiments, Compound No. 1 or the pharmaceutically acceptable salt thereof is administered once weekly in about the first 28 days, and is administered once weekly for the first three weeks in about every 28 days thereafter; and Compound A or the pharmaceutically acceptable salt thereof is administered once weekly in about the first 28 days, and is administered once weekly for the first three weeks in about every 28 days thereafter.

Exemplary Embodiments Related to Compound No. 1, Ruxolitinib, and Compound A

In some aspects, the present disclosure provides a combination comprising:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a method of treating or preventing cancer in a subject, comprising administering to the subject:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a method of treating or preventing myelofibrosis in a subject, comprising administering to the subject:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a combination for treating or preventing cancer in a subject, wherein the combination comprises:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a combination for treating or preventing myelofibrosis in a subject, wherein the combination comprises:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides use of a combination in the manufacture of a medicament for treating or preventing cancer in a subject, wherein the combination comprises:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides use of a combination in the manufacture of a medicament for treating or preventing myelofibrosis in a subject, wherein the combination comprises:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides Compound No. 1 or a pharmaceutically acceptable salt thereof for use in combination with ruxolitinib or a pharmaceutically acceptable salt thereof, and Compound A or a pharmaceutically acceptable salt thereof, in treating or preventing cancer in a subject.

In some aspects, the present disclosure provides Compound No. 1 or a pharmaceutically acceptable salt thereof for use in combination with ruxolitinib or a pharmaceutically acceptable salt thereof, and Compound A or a pharmaceutically acceptable salt thereof, in treating or preventing myelofibrosis in a subject.

In some aspects, the present disclosure provides ruxolitinib or a pharmaceutically acceptable salt thereof for use in combination with Compound. No. 1 or a pharmaceutically acceptable salt thereof, and Compound A or a pharmaceutically acceptable salt thereof, in treating or preventing cancer in a subject.

In some aspects, the present disclosure provides ruxolitinib or a pharmaceutically acceptable salt thereof for use in combination with Compound No. 1 or a pharmaceutically acceptable salt thereof, and Compound A or a pharmaceutically acceptable salt thereof, in treating or preventing myelofibrosis in a subject.

In some aspects, the present disclosure provides Compound A or a pharmaceutically acceptable salt thereof for use in combination with Compound No. 1 or a pharmaceutically acceptable salt thereof, and ruxolitinib or a pharmaceutically acceptable salt thereof, in treating or preventing cancer in a subject.

In some aspects, the present disclosure provides Compound A or a pharmaceutically acceptable salt thereof for use in combination with Compound No. 1 or a pharmaceutically acceptable salt thereof, and ruxolitinib or a pharmaceutically acceptable salt thereof, in treating or preventing myelofibrosis in a subject.

In some aspects, the present disclosure provides a method of treating or preventing cancer in a subject, wherein the cancer is resistant to treatment with a JAK inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a method of treating or preventing myelofibrosis in a subject, wherein the myelofibrosis is resistant to treatment with a JAK inhibitor (e.g., ruxolitinib or a pharmaceutically acceptable salt thereof) alone, the method comprising administering to the subject:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a combination for treating or preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides a combination for treating or preventing myelofibrosis in a subject, wherein the myelofibrosis is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides use of a combination in the manufacture of a medicament for treating or preventing cancer in a subject, wherein the cancer is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides use of a combination in the manufacture of a medicament for treating or preventing myelofibrosis in a subject, wherein the myelofibrosis is resistant to treatment with a JAK inhibitor (e.g., ruxolitinib or a pharmaceutically acceptable salt thereof) alone, the combination comprising:

(i) a pharmaceutically effective amount of Compound No. 1 or a pharmaceutically acceptable salt thereof;

(ii-a) a pharmaceutically effective amount of ruxolitinib or a pharmaceutically acceptable salt thereof; and (ii-b) a pharmaceutically effective amount of Compound A or a pharmaceutically acceptable salt thereof.

In some aspects, the present disclosure provides Compound No. 1 or a pharmaceutically acceptable salt thereof for use in combination with ruxolitinib or a pharmaceutically acceptable salt thereof, and Compound A or a pharmaceutically acceptable salt thereof, in treating or preventing cancer in a subject, wherein the cancer is resistant to treatment with a JAK inhibitor (e.g., ruxolitinib or a pharmaceutically acceptable salt thereof) alone.

In some aspects, the present disclosure provides Compound No. 1 or a pharmaceutically acceptable salt thereof for use in combination with ruxolitinib or a pharmaceutically acceptable salt thereof, and Compound A or a pharmaceutically acceptable salt thereof, in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides ruxolitinib or a pharmaceutically acceptable salt thereof for use in combination with Compound No. 1 or a pharmaceutically acceptable salt thereof, and Compound A or a pharmaceutically acceptable salt thereof, in it) treating or preventing cancer in a subject, wherein the cancer is resistant to treatment with a JAK inhibitor (e.g., ruxolitinib or a pharmaceutically acceptable salt thereof) alone.

In some aspects, the present disclosure provides ruxolitinib or a pharmaceutically acceptable salt thereof for use in combination with Compound No. 1 or a pharmaceutically acceptable salt thereof, and Compound A or a pharmaceutically acceptable salt thereof, in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides Compound A or a pharmaceutically acceptable salt thereof for use in combination with Compound No. 1 or a pharmaceutically acceptable salt thereof, and ruxolitinib or a pharmaceutically acceptable salt thereof, in treating or preventing cancer in a subject, wherein the cancer is resistant to treatment with a JAK inhibitor (e.g., ruxolitinib or a pharmaceutically acceptable salt thereof) alone.

In some aspects, the present disclosure provides Compound A or a pharmaceutically acceptable salt thereof for use in combination with Compound No. 1 or a pharmaceutically acceptable salt thereof, and ruxolitinib or a pharmaceutically acceptable salt thereof, in treating or preventing myelofibrosis in a subject, wherein the myelofibrosis is resistant to treatment with a JAK inhibitor (e.g., ruxolitinib or a pharmaceutically acceptable salt thereof) alone.

In some aspects, the present disclosure provides a method of treating or preventing cancer in a subject, wherein a JAK mutation (e.g., V617F) is identified in the subject (e.g., in a biological sample from the subject), comprising administering to the subject:

(i) a pharmaceutically effective amount of Compound No. 1 or a pharmaceutically acceptable salt thereof;
(ii-a) a pharmaceutically effective amount of ruxolitinib or a pharmaceutically acceptable salt thereof; and
(ii-b) a pharmaceutically effective amount of Compound A or a pharmaceutically acceptable salt thereof.

In some aspects, the present disclosure provides a method of treating or preventing cancer in a subject, comprising:

(a) identifying the presence of a JAK mutation (e.g., V617F) in the subject (e.g., in a biological sample from the subject); and
(b) administering to the subject:
  (i) a pharmaceutically effective amount of Compound No. 1 or a pharmaceutically acceptable salt thereof;
  (ii-a) a pharmaceutically effective amount of ruxolitinib or a pharmaceutically acceptable salt thereof; and
  (ii-b) a pharmaceutically effective amount of Compound A or a pharmaceutically acceptable salt thereof.

In some embodiments, Compound No. 1 or the pharmaceutically acceptable salt thereof is administered at a dosage (e.g., a weekly dosage) of about 80 mg, about 160 mg, or about 240 mg; and Compound A or the pharmaceutically acceptable salt thereof is administered at a dosage (e.g., a weekly dosage) of about 30 mg or about 45 mg.

In some embodiments, Compound No. 1 or the pharmaceutically acceptable salt thereof is administered once weekly in about the first 28 days, and is administered once weekly for the first three weeks in about every 28 days thereafter; Compound A or the pharmaceutically acceptable salt thereof is administered once weekly in about the first 28 days, and is administered once weekly for the first three weeks in about every 28 days thereafter; and ruxolitinib or a pharmaceutically acceptable salt thereof (e.g., a mesylate salt of ruxolitinib) is not administered in about the first 28 days, and is administered twice daily thereafter.

Pharmaceutical Compositions and Kits in some aspects, the present disclosure provides a pharmaceutical composition comprising a combination disclosed herein and one or more pharmaceutically acceptable carriers or excipients.

In some aspects, the present disclosure provides a pharmaceutical composition comprising:

(i) a pharmaceutically effective amount of Compound No. 1 or a pharmaceutically acceptable salt thereof;
(ii) at least one additional therapeutic agent (e.g., paclitaxel, osimertinib, ruxolitinib, Compound A, or a pharmaceutically acceptable salt thereof); and
(iii) one or more pharmaceutically acceptable carriers or excipients.

In some aspects, the present disclosure provides a pharmaceutical kit comprising a combination disclosed herein.

In some aspects, the present disclosure provides a pharmaceutical kit comprising:

(i) a pharmaceutically effective amount of Compound No. 1 or a pharmaceutically acceptable salt thereof; and
(ii) at least one additional therapeutic agent (e.g., paclitaxel, osimertinib, ruxolitinib, Compound A, or a pharmaceutically acceptable salt thereof).

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELI" (BASF, Parsippany, N.J.) or phosphate buffered saline (PBS), In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition.

Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared to according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease.

It is understood that the pharmaceutical compositions can be included in a container, pack, or dispenser together with instructions for administration.

Definitions

As used herein, the term "about" refers to a range covering any normal fluctuations appreciated by one of ordinary skill in the relevant art. In some embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "Janus kinase inhibitor" or "JAK inhibitor" refers to an agent which is capable of inhibiting the activity of one or more of the Janus kinase family of enzymes (e.g., JAK1, JAK2, and/or JAK3) and/or is capable of interfering with the JAK-STAT signaling pathway. In some embodiments, the JAK inhibitor is ruxolitinib, tofacitinib, oclacitinib, baricitinib, peficitinib, fedratinib, upadacitinib, filgotinib, cerdulatinib, gandotinib, lestaurtinib, momelotinib, pacritinib, abrocitinib, a pharmaceutically acceptable salt thereof, or a prodrug thereof.

It is understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

It is understood that the compounds of the present disclosure, for example, the salts of the compounds, can exist in either hydrated or unhydrated (the anhydrous) form or as solvates with other solvent molecules. Nonlimiting examples of hydrates include monohydrates and dihydrates. Nonlimiting examples of solvates include ethanol solvates and acetone solvates.

As used herein, the expressions "one or more of A, B, or C," "one or more A, B, or C." "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith. M. B., March, J., *March's Advanced Organic Chemistry: Reactions, Mechanisms, and Structure,* $5^{th}$ edition, John Wiley & Sons: New York, 2001; Greene, T. W., Nuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In some embodiments, the mammal is a human.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "temporal proximity" refers to that administration of one therapeutic agent (e.g., Compound No. 1) occurs within a time period before or after the administration of another therapeutic agent (e.g., paclitaxel, osimertinib, ruxolitinib. Compound A, or a pharmaceutically acceptable salt thereof), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

It is understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like, Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the terra "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric; polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is understood that all references to pharmaceutically acceptable salts include solvent addition forms (solvates) or crystal forms (polymorphs) as defined herein, of the same salt.

As used herein, the term "prodrug" refers to any agent which, when administered to a mammal, is converted in whole or in part to a targeted compound. In some embodiments, the prodrug of a compound is also a pharmaceutically acceptable salt of the compound.

It is understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Study of Combination of Compound No. 1 and Paclitaxel in Patients with Relapsed/Refractory Small Cell Lung Cancer A multi-center, open-label, phase I/II study of combination therapy with Compound No. 1 plus paclitaxel in patients with relapsed. SCLC was performed.

The phase 1 portion was performed using TITE-CRM methodology to determine the MTD of Compound No. 1 with a fixed dose of paclitaxel. The phase II portion utilized a Simon two-stage design to determine the efficacy of the combination therapy with response rate as the primary endpoint. Upon enrollment, patients underwent a comprehensive history and physical exam, along with baseline laboratory assessment. Baseline CT imaging was required within 4 weeks prior to study entry. Biopsy of the primary tumor or a metastatic lesion was encouraged at baseline, prior to initiation of therapy, for correlative biomarker and pharmacodynamic studies.

In the phase 1 portion, eligible patients received Compound No. 1 at the selected dose-level on days 1, 8 and 15 plus a fixed-dose of paclitaxel 80 mg/m$^2$ on days 1 and 8 of a 21-day cycle. There were four dose-levels of Compound No. 1 (180 mg, 240 mg, 320 mg, and 400 mg) with the first patient starting at dose-level of 240 mg and subsequent patients increasing dose-levels as determined by the TITE-CRM methodology. There was no intra-patient dose-escalation. Patients were continuously assessed for adverse events, including DLTs which are further describe herein. Response assessment by CT imaging occurred every 2 cycles and treatment continued until progression of disease, unacceptable toxicity, or patient preference to stop.

In the phase II portion, eligible patients received Compound No. 1 at the MTD determined in the phase 1 portion on days 1, 8 and 15 plus paclitaxel 80 mg/m$^2$ on days 1 and 8 of a 21-day cycle. Response assessment by CT imaging occurred every 2 cycles and treatment continued until progression of disease, unacceptable toxicity, or patient preference to stop.

Patent Eligibly Criteria

- Ages Eligible for Study: 18 years to 100 years

Inclusion Criteria:

- Histologically or cytologically confirmed SCLC;
- Progression of disease on or after initial treatment with platinum-based therapy with or without thoracic radiotherapy; patients may have also received prior immunotherapy or other chemotherapy agents, except for paclitaxel; there is no limit on the number of prior treatment regimens allowed,
- Male or non-pregnant, non-lactating female patients age ≥ 18 years;
- Eastern Cooperative Oncology Group (ECOG) performance status 0-2;
- Adequate hematologic function as indicated by:
  - Platelet count ≥ 100,000/mm3
    - Note: Use of transfusions or thrombopoietic agents to achieve baseline platelet count criterion is prohibited.
  - Hemoglobin ≥ 9.0 g/dL
  - Absolute neutrophil count (ANC) ≥ 1000/μL. Note: Use of growth-factors to maintain ANC criterion prior to enrollment is not permitted,
- Adequate renal and liver function as indicated by:
  - Serum creatinine ≤ 1.5×upper limit of normal (ULN); if serum creatinine is >1.5×ULN, creatinine clearance must be ≥ 50 mL/min.
  - Total bilirubin ≤ 1.5×ULN; If patient has Gilbert's syndrome, may have bilirubin>1.5×ULN
  - Aspartate aminotransferase (AST) and alanine aminotransferase (ALT) ≤ 3×ULN; for patients with known liver metastases, AST and ALT may be ≤ 5×ULN.
  - Coagulation: aPTT and PT ≤ 1.2×ULN
- Patients with previously treated, clinically controlled brain metastases are allowed. Clinically controlled is defined as surgical excision and/or radiation therapy followed by at least 14 days of stable neurologic function and no evidence of CNS disease progression as determined by CT or MRI within 14 days prior to study enrollment. Continued use of corticosteroids is permissible.
- Willingness to use contraception by a method that is deemed effective by the investigator by both males and female patients of child bearing potential and their partners throughout the treatment period and for at least three months following the last dose of study drug; see section 7.4 for contraceptive methods (postmenopausal women must have been amenorrheic for at least 12 months to be considered of non-childbearing potential).
- Able to understand and willing to sign a written informed consent form
- Able and willing to comply with study procedures and follow-up examination.

Inclusion Criteria:

- Receiving concurrent anti-cancer therapy (chemotherapy, radiation therapy, surgery, immunotherapy, hormonal therapy, targeted therapy, biologic therapy) or any investigational therapy within 14 days prior to the first dose of treatment, with the exception of hormones for hypothyroidism, estrogen replacement therapy (ERT), anti-estrogen analogs, or agonists required to suppress serum testosterone levels.
- Continuance of toxicities due to prior treatment that do not recover to <grade 2, except for clinically insignificant toxicities such as lymphopenia or alopecia.
- Known bleeding diathesis/disorder.
- Recent history of non-chemotherapy induced thrombocytopenia associated a major bleeding episode within 1 year prior to study entry,
- Active immune thrombocytopenic purpura (ITP), active autoimmune hemolytic anemia (AIHA), or a history of being refractory to platelet transfusions, within 1 year prior to the first dose of study drug.
- Serious gastrointestinal bleeding within 3 months of study entry; 7. Use of therapeutic doses of anticoagulants is an exclusion, including anti-platelet agents. Use of low-dose anticoagulation medications to maintain the patency of a central intravenous catheter or aspirin (<100 mg) for cardiovascular protection are permitted.

- Failure to recover adequately from prior surgical procedures, as judged by the investigator. Patients who have had major surgery within 28 days from study entry, and patients who have had minor surgery within 14 days of study entry are excluded. (Minor surgery is invasive operative procedure involving resecting skin or mucus membranes and connective tissue. Major surgery is an invasive operative procedure involving more extensive resection, such as body cavity opening or organ resection.)
- Unstable angina, myocardial infarction, or a coronary revascularization procedure within 180 days of study entry.
- Active symptomatic fungal, bacterial and/or viral infection including, but not limited to, active human immunodeficiency virus (HIV) or viral hepatitis (B or C); testing for hepatitis B and C is not required for study enrollment.
- Uncontrolled concurrent illness that would limit compliance with the study requirements, including, but not limited to: serious uncontrolled infection, symptomatic congestive heart failure, unstable angina pectoris, cardiac arrhythmia, or psychiatric illness.
- Prior treatment with a Bcl-2/Bcl-xL inhibitor.
- Prior treatment with paclitaxel.

Example 2. Study of Combination of Compound No. 1 and Osimertinib in Patients with EGER-TKI-Resistant Non-Small-Cell Lung Cancer A multi-center, open-label, Phase 1 b study evaluating the adverse events and best dose of the combination of Osimertinib with Compound No. 1 in EGFR-TKI-resistant NSCLC patients was performed.

In exploration phase, 3+3 design was used to determine the MTD/RP2D of the combination of Osimertinib with Compound No. 1; Dose of Osimertinib was fixed at 80 mg QD. Dose of Compound No. 1 started with 240 mg weekly, then escalated to 320 mg weekly and 400 mg weekly or declined to 160 mg weekly and 80 weekly if the patient did not tolerate to 240 mg weekly dosage.

In expansion phase, IF 1 confirmed PR or CR observed in NSCLC patients who failed 3rd generation EGFR TKI, the exploration of the combination of osimertinib with Compound No. 1 in 3rd generation EGFR TKI naïve NSCLC patients was initiated. Patients were treated in 21-day cycles. Compound No. 1 was administered via intravenous infusion for 30 minutes weekly (at day 1, day 8, and day 15), and osimertinib was orally administered daily at 80 mg.

Patent Eligibility Criteria

Ages Eligible for Study: 18 years to 100 years

Inclusion Criteria:

- Histologically or cytologically confirmed incurable advanced or metastatic non-small cell lung cancer.
- At least 1 measurable lesion (RECIST 1.1)
- Confirmed EGFR mutation positive before start use prior EGFR TKI (s).
- Willing to biopsy or to supply achieved tumor sample which biopsy after the most recent treatment.
- Male or female patients age ≥ 18 years.
- Eastern Cooperative Oncology Group (ECOG) Performance Status 0-1.
- Estimated OS ≥ 3 months.
- Adequate hematologic and bone marrow functions.
- Adequate renal and liver function.
- Brain metastases with clinically controlled neurologic symptoms.
- Had recovered from all toxicities related to prior anticancer therapies to grade ≤ 2, except for patients with grade 2 nausea/vomiting and/or grade 2 diarrhea despite optimal supportive therapy who will not be allowed to participate in the study.
- Willingness to use contraception by a method that is deemed effective by the investigator by both males and female patients of child bearing potential (postmenopausal women must have been amenorrhea for at least 12 months to be considered of non-childbearing potential) and their partners throughout the treatment period and for at least three months following the last dose of study drug.
- Ability to understand and willingness to sign a written informed consent form (the consent form must be signed by the patient prior to any study-specific procedures).
- Willingness and ability to comply with study procedures and follow-up examination.

Exclusion Criteria:

- Received chemotherapy, radiation therapy, surgery, immunotherapy, hormonal therapy, targeted therapy, biologic therapy (hormones for hypothyroidism or estrogen replacement therapy (ERT), anti-estrogen analogs, agonists required to suppress serum testosterone levels are permitted); or any investigational therapy, or has had tumor embolization or tumor lysis syndrome (TLS) within 28 days prior to the first dose of study drug, received TKIs within 14 days.
- A history of interstitial lung disease, drug-induced interstitial lung disease, radiation pneumonitis requiring steroid therapy, or any evidence of clinically active interstitial lung disease.
- Any of the following cardiac criteria: mean value of QTcB for three resting periods during the screening period>470 milliseconds; rhythm of resting electrocardiogram (ECG), any clinically important abnormality of conduction or morphology (e.g., complete left bundle branch block, Grade 3 heart block, Grade 2 heart block); family history of congenital long QT prolongation syndrome or long QT syndrome.
- Evidence of any serious or uncontrolled systemic disease; various chronic active infections such as hepatitis B (HBV-DNA ≥ 104 copy number/ml or 2000 IU/ml), hepatitis C and HIV; uncontrollable Hypertensive patients (requires 2 or more drugs to control blood pressure); unstable angina; angina pectoris within 3 months prior to study;
- congestive heart failure (NYHA class II or higher); myocardial infarction (NSTEMI or STEMI) history in 6 months before study enrollment; severe arrhythmia requiring medical attention; severe liver, kidney, gastrointestinal or metabolic diseases.
- Patients who are unable to stop taking the drug or herbal medicine within 1 week before the first study drug treatment and during the treatment phase (these drugs or herbs are known to be effective inducers of cytochrome PH450 or effective inhibitors or inducers of CYP3A4); Patients who discontinue use of these compounds at least 1 week prior to receiving this regimen are eligible.
- Hemorrhagic constitution disease, such as a history of non-chemotherapy-induced thrombocytopenic hemorrhage or a history of ineffective platelet transfusion within 1 year prior to the first dose of study drug;

- Severe gastrointestinal bleeding occurred within 3 months prior to the first dose of study drug; Active immune thrombocytopenic purpura (ITP), active autoimmune hemolytic anemia (AIHA), etc.
- Use a therapeutic dose of anticoagulant or antiplatelet agent before the first use of Compound No. 1 or within 7 days of central catheter placement (if platelet count is stable (≥50×109/L), Subjects who previously received aspirin to prevent thrombosis therapy can reuse low-dose aspirin (i.e., up to 100 mg QD) after 3 weeks of study drug treatment; Decisions regarding anticoagulants and antiplatelet therapy will be determined by the investigator and the sponsor; Allow low-dose anticoagulant drugs to maintain central venous catheters open.
- Received a biologic (G-CSF, GM-CSF or erythropoietin) within 28 days prior to the first dose of study drug.
- According to the investigator's judgment; patients who did not fully recover after surgery. Patients who underwent major surgery within 28 days prior to the first study drug and who underwent minor surgery within 7 days prior to the start of the study.
- Other malignancies have been diagnosed within 5 years prior to the first use of the study drug; except effectively treated skin basal cell carcinoma, cutaneous squamous cell carcinoma, and/or effectively resected orthotopic cervical cancer and/or breast Cancer.
- Female patients during pregnancy or lactation.
- Previous allergies or intolerance to treatment with osimertinib.
- A diagnosis of febrile neutropenia within one week prior to the first use of the study drug.
- Prior treatment with Bcl-2/Bcl-xL inhibitors.
- Any other condition or circumstance of that would, in the opinion of the investigator, make the patient unsuitable for participation in the study.

Example 3. Study of Combination of Compound No. 1 with Ruxolitinib and/or Compound a in Patients with Myelofibrosis A Phase I/II, open-label, multi-center "umbrella" study was performed for evaluating the tolerability and clinical activity of Compound No. 1 plus ruxolitinib; Compound No. 1 plus ruxolitinib and Compound A in myelofibrosis patients with suboptimal response to JAK2 inhibitor; and Compound No. 1 plus Compound A in patients who are refractory or intolerant to FDA approved JAK2 inhibitor (ruxolitinib and fedratinib), For the design of this study, see FIG. 1.

The study was an umbrella design focused on previously treated myelofibrosis patients divided into two treatment groups, based on their potential to benefit from JAK2 inhibitors. Group 1 is myelofibrosis patients that could benefit when the novel agent Compound No. 1 or When Compound No. 1 plus Compound A are added to ruxolitinib therapy and Group 2 is patients that cannot tolerate ruxolitinib or fedratinib or are resistant to JAK2i therapy. The primary objective of the Phase I is to characterize the safety and determine the MTD/RP2D of Compound No. 1 when combined with ruxolitinib; when combined with ruxolitinib and Compound A; and when the 2 novel agents Compound No. 1 and Compound A are combined. The primary endpoint of the Phase II is to obtain preliminary efficacy by evaluating the disease control based on reduction in spleen size (≥35% reduction in volume as determined by MRI or CT scan) or myelofibrosis associated symptoms (≥50% reduction in total symptom score, assessed using Myelofibrosis Symptom Assessment Form, Mesa et al 2009) when Compound No. 1 is combined with ruxolitinib; or combined with ruxolitinib and Compound A; and when the 2 novel agents Compound No. 1 and Compound A are combined as therapy for patients with pretreated myelofibrosis. Patients in Group 1 were treated in Part 1 (combination of Compound No. 1 plus ruxolitinib) and Part 2 (combination of Compound. No. 1 plus ruxolitinib plus Compound A). In Part 1 the MTD dose determination of Compound No. 1 plus dose of ruxolitinib per package insert will be conducted using a standard 31-3 dose escalation followed by a dose expansion cohort at the MTD/RP2D. Part 2 will commence after discussion between sponsor and investigators. In Part 2, two cohorts of Compound A doses were tested one (a) at 30 mg and another (b) at 45 mg in combination with Compound No. 1 plus ruxolitinib at their MTD/RP2D. Each of these cohorts will accrue up to 15 patients, Patients in Group 2 (myelofibrosis patients who are intolerant or refractory to JAK2i) were treated in Part≥3 once 3 patients treated at ≥30 mg Compound A plus Compound No. 1 and ruxolitinib is considered safe and tolerated. Depending on the individual doses of Compound No. 1 and Compound A in the combination with ruxolitinib the combination doses of Compound No. 1 and Compound A as dual agents may be increased but to no more than 240 mg for Compound No. 1 and no more than 45 mg for Compound A.

Group 1. Group 1 consisted of patients currently undergoing or who have undergone prior treatment with a JAK2 inhibitor achieving/achieved suboptimal response or are unlikely to achieve optimal response if they continue with a JAK2 inhibitor. In this study patients were considered to have achieved suboptimal benefit from JAK2 inhibitors if. (1) during treatment with JAK2 inhibitors they achieve some therapeutic benefit including spleen size reduction and/or myelofibrosis symptoms reduction but fall short of optimal benefit such as less than 35% spleen reduction or have not achieved substantial symptom control at ≤24 weeks and are considered unlikely to achieve optimal benefit if they were to continue treatment (such as patients who have dose reduction for adverse events before having achieved optimal benefit).

Part 1. The study design was, 3+3 dose-escalation, of Compound No. 1 administered once weekly for 4 weeks (induction) followed by once weekly for 3 weeks and one week off. The starting dose for Compound No. 1 was 160 mg added to ruxolitinib dose per package insert. The Compound No. 1 dose may be escalated to a maximum of 240 mg or de-escalated to the lowest dose of 80 mg depending on tolerability. At the MTD/RP2D expansion cohorts up to 15 patients were allowed. If the proportion of patients achieving ≥35% reduction in spleen volume in the expansion cohort of 15 is 30% at 24 weeks additional patients up to 30 may be added to further characterize response and safety.

Treatment Schedule for Part 1. Patients starting Compound No. 1 treatment in addition to ruxolitinib were on ruxolitinib daily dose for at least 5 days at the same dose they are to take in combination with Compound No. 1. Compound No. 1 was administered as intravenous infusion each over 30 minutes during weeks 1 to 4 and thereafter weekly for 3 weeks followed by one week off. Thus, a treatment cycle was 28 days and during Cycle 2 and subsequent cycles patients received Compound No. 1 once weekly for 3 weeks with one week off Ruxolitinib was taken orally twice a day as per package insert.

Part 2. At the MTD/RP2D of Compound No. 1 plus ruxolitinib two doses of Compound A (30 mg and 45 mg) were tested in 2 cohorts of up to 15 each to characterize safety and efficacy. The first combination was with Compound No. 1 plus ruxolitinib at RP2D plus Compound A at 30 mg and once 3 patients are treated and considered to acceptable safety the next cohort of Compound. No, 1 plus ruxolitinib plus Compound A at 45 mg was allowed. Following completion of at least one 28-day cycle for first 3 patients in each cohort alternate addition of a patient to each cohort was allowed up to a maximum of 15 patients in each cohort.

Treatment Schedule for Part 2, Both Compound No. 1 and Compound. A were administered as intravenous infusion each over 30 minutes during weeks 1 to 4 and thereafter weekly for 3 weeks followed by one week off. Thus, a treatment cycle was 28 days and during Cycle 2 and subsequent cycles patients received both Compound No. 1 and Compound A once weekly for 3 weeks with one week off. Compound A was given ahead of Compound No. 1 after an intravenous flush with 100-150 mL of normal saline. Ruxolitinib will be taken orlay twice a day per package insert.

Group 2—Part 3. Part 3 was conducted in patients in Group 2. Patients in Group 2 were those that are not candidates for JAK2 inhibitors as they are refractory to JAK2 inhibitors, defined as having progressed, during or within six (6) months of discontinuing FDA approved JAK2 inhibitor therapy; or are intolerant (unable to tolerate adverse effects at clinically recommended doses) to FDA approved JAK2 inhibitors. Treatment in this cohort started once at least 3 patients in part 2 (cohort of patients in the combination of Compound No. 1 plus ruxolitinib plus Compound A) have completed. The starting doses of the combination depended on the doses of Compound No. 1 plus Compound. A considered well tolerated when both are combined with ruxolitinib. Two potential scenarios are described below:

Scenario 1: Compound No. 1 at 240 mg plus Compound A at 45 mg plus the standard dose of ruxolitinib were tolerated, the dose of Compound No. 1 was 240 mg and of Compound A was 45 mg in the combination and no dose escalation occurred.

Scenario 2: Compound No. 1 at 80 mg plus Compound A at 20 mg plus the standard dose of ruxolitinib were the MTD, the dose of Compound No. 1 started at 160 mg and of Compound A was 45 mg in the combination. The dose of Compound No. 1 may be escalated to 240 mg and no more or be de-escalated to 80 mg and no lower. The doses of Compound A may be adjusted after discussion between investigators and sponsor.

Treatment Schedule for Part 3. Both Compound No. 1 and Compound A were administered as intravenous infusions each over 30 minutes during Cycle 1 (weeks 1 to 4) and in Cycle 2 and thereafter, weekly for 3 weeks followed by one week off. Thus, a treatment cycle will be 28 days and during Cycle 2 and subsequent cycles patients received both Compound No. 1 and Compound A once weekly for 3 weeks with one week off. When the 2 novel agents are administered on the same day, Compound A will be given ahead of Compound No. 1 after an intravenous flush with 100-150 mL of normal saline.

Figure 2A:
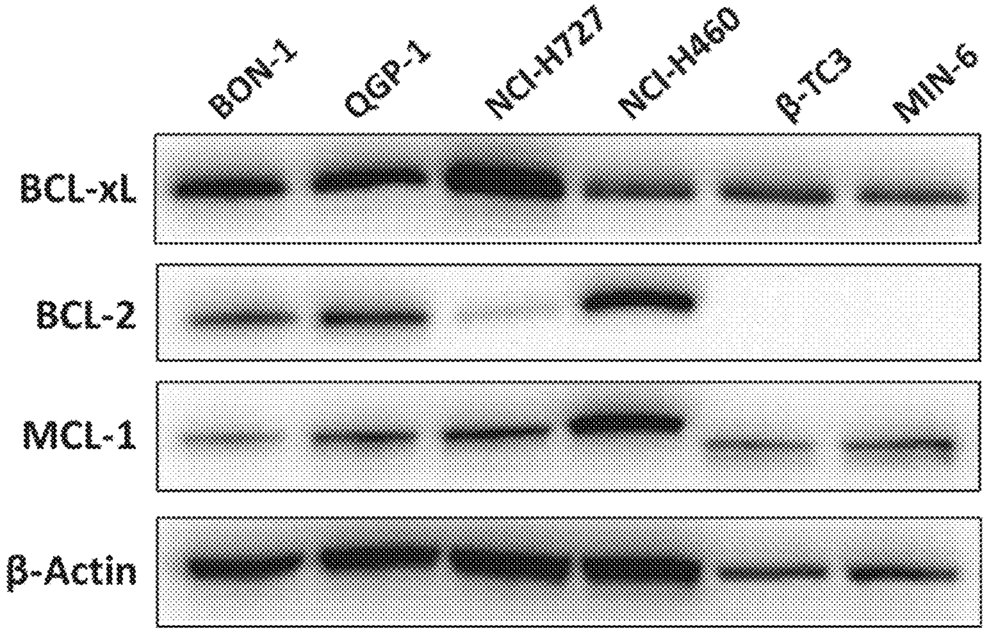
FIGS. 2A and 2B are a set of graphs showing the BCL-2 family member protein levels in six NEN cell lines.
Figure 2B:
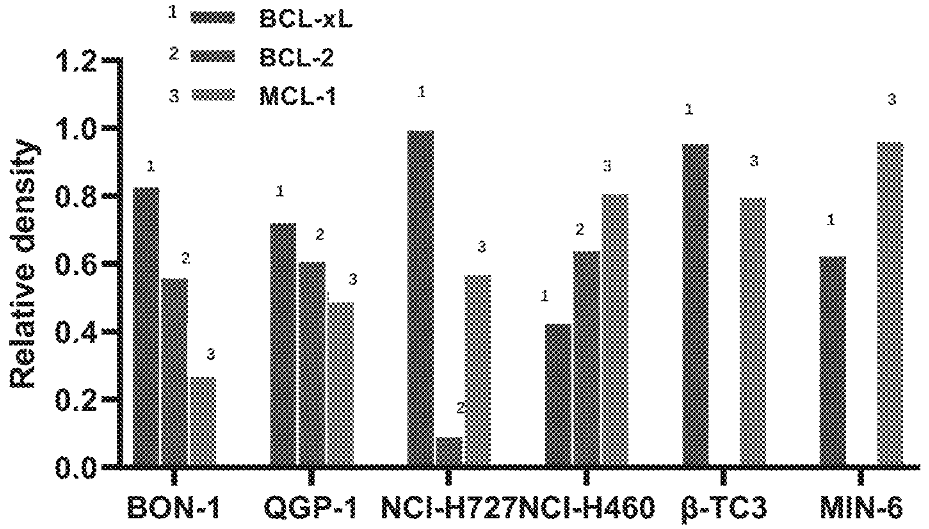
Figure 3A:
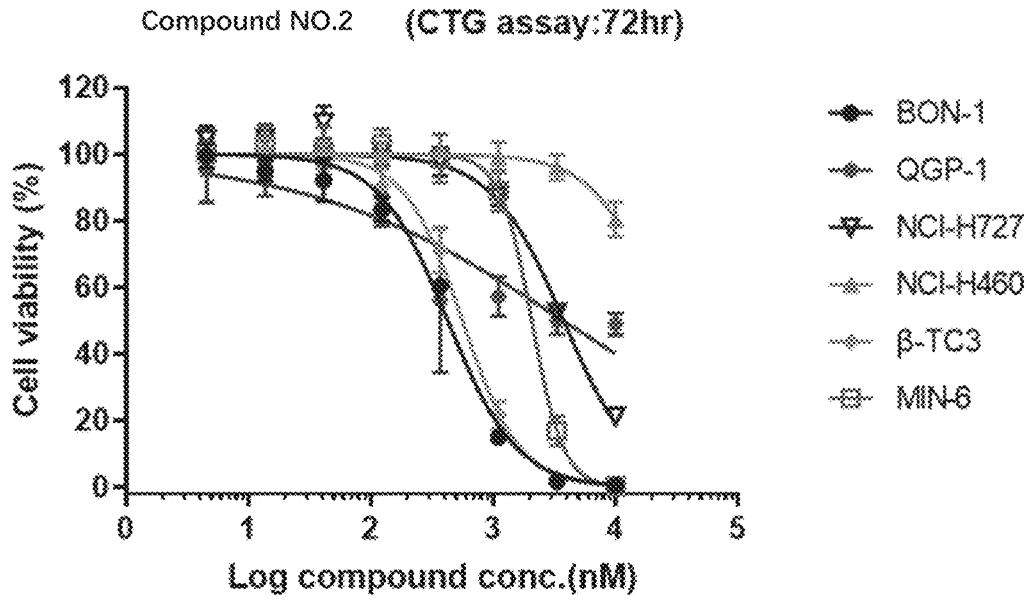
FIGS. 3A and 3B are a set of graphs showing the cell viability/CTG assays for NEN cell lines treated with BCL-2/xL inhibitor Compound No. 2 (an active metabolite of Compound No. 1)(FIG. 3A) or ABT-263 (FIG. 3B).
Figure 3B:
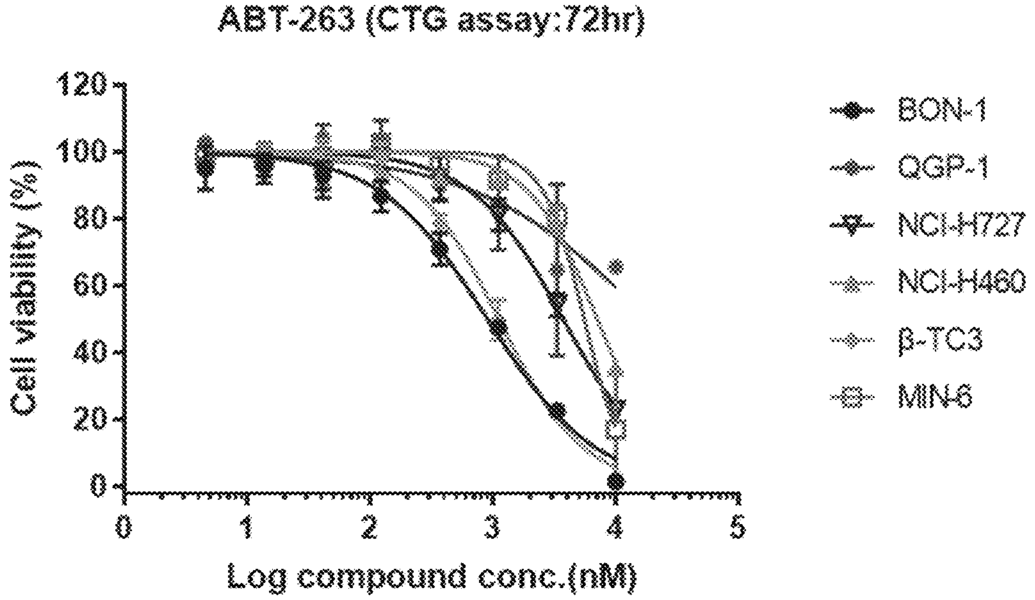

Example 4. Assessment of Compound No. 1 in Overcoming Apoptotic Blockade in Neuroendocrine Neoplasm The activity of Compound No. 2 (an active metabolite of Compound No. 1) in overcoming apoptotic blockade in neuroendocrine neoplasm was tested, alone or in comparison with ABT-263. High expression of BCL-xL protein was found in NEN cell lines (see FIGS. 2A and 2B), and it was observed that Compound No. 2 inhibits the NEN cell viability (see FIGS. 3A and 3B, and Table A below).

TABLE A

| $IC_{50}$ (μM, CTG assay: 72 hr)* | | |
|---|---|---|
| Cell Lines | Compound No. 2 | ABT-263 |
| BON-1 | 0.43 | 0.91 |
| QGP-1 | 3.78 | 10 |
| NCI-H727 | 3.79 | 3.74 |
| NCI-H460 | 10 | 71 |
| β-TC3 | 0.55 | 1.12 |
| MIN-6 | 2.07 | 5.56 |

*The values are approximate and are subject to experimental and instrumental variations.

Figure 4A:
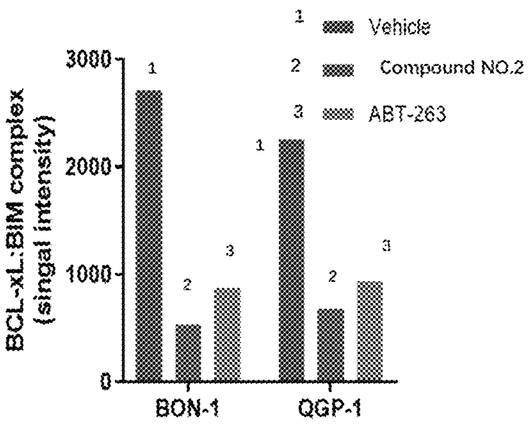
FIGS. 4A-4C are a set of graphs showing the BCL-2 family member complex intensity in BON-1 and QGP-1 treated with BCL-2/xL inhibitors
Figure 4B:
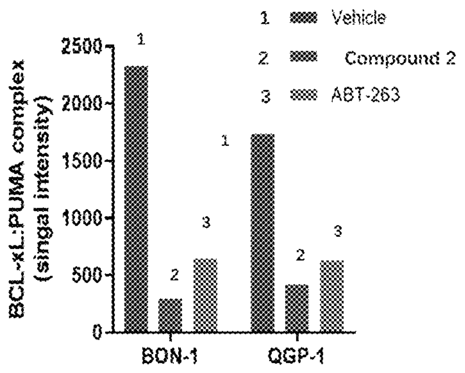
Figure 4C:
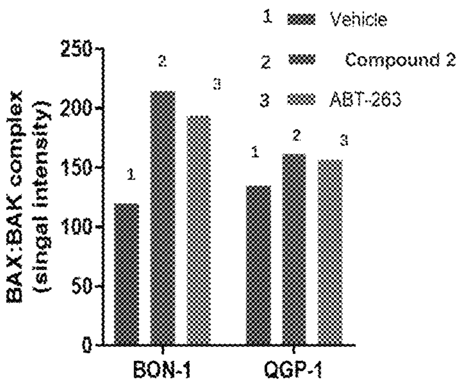
Figure 5A:
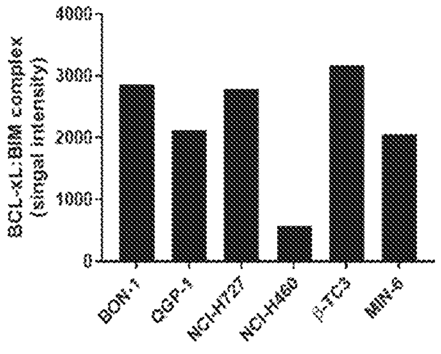
FIGS. 5A-5C and 6A-6C are a set of graphs showing the correlation between baseline BCL-xL:BIM/P/UMA or MCL-1:BIM complex level with Compound No. 2 (an active metabolite of Compound No. 1) $IC_{50}$ values.
Figure 5B:
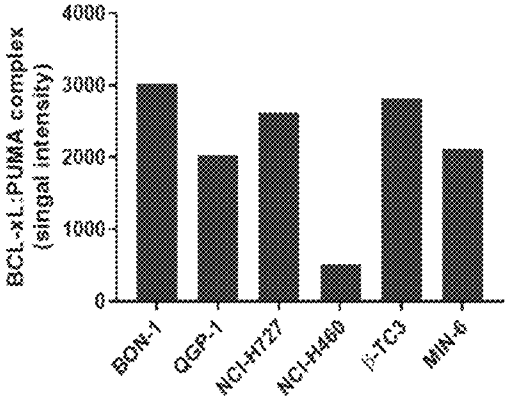
Figure 5C:
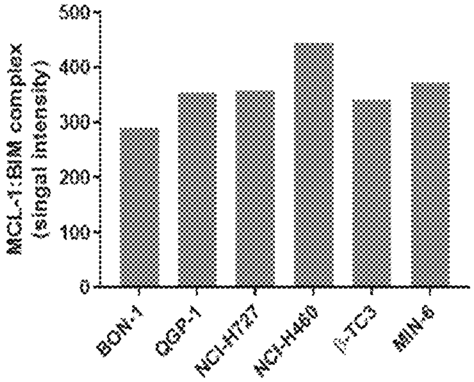
Figure 6A:
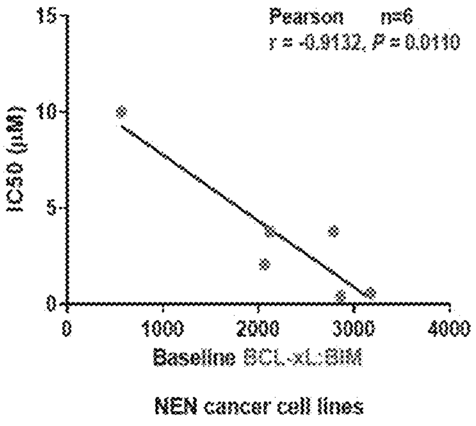
Figure 6B:
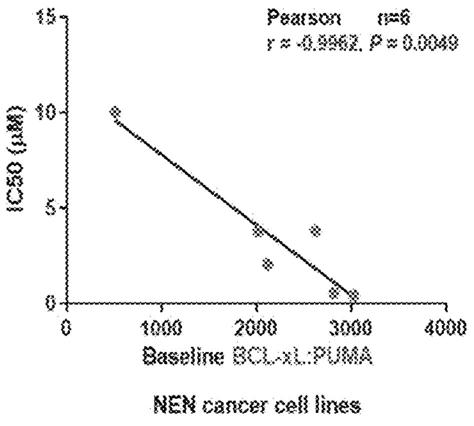
Figure 6C:
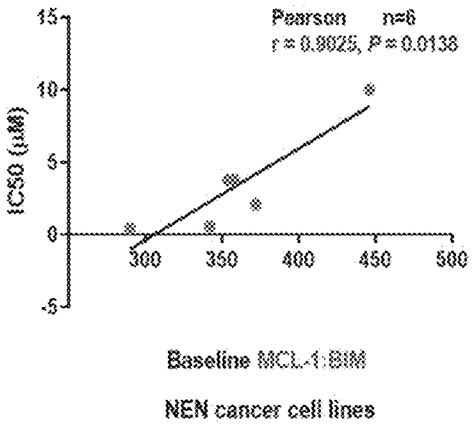

It was further observed that Compound No. 2 decreases BCL-xL:BIM complex, and increases BAX:BAK complex, to trigger apoptosis (see FIGS. 4A-4C). Finally, higher BCL-xL, but lower MCL-1, complex intensity showed better sensitivity for Compound No. 2 (see FIGS. 5A-5C and 6A-6C).

EQUIVALENTS

It is understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein

What is claimed is:

1. A method of treating cancer in a subject, comprising administering to the subject:

(Compound No. 1)

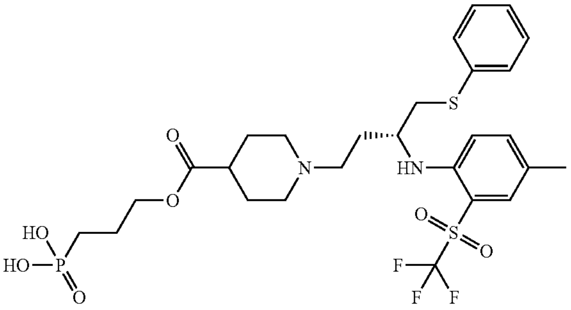

-continued

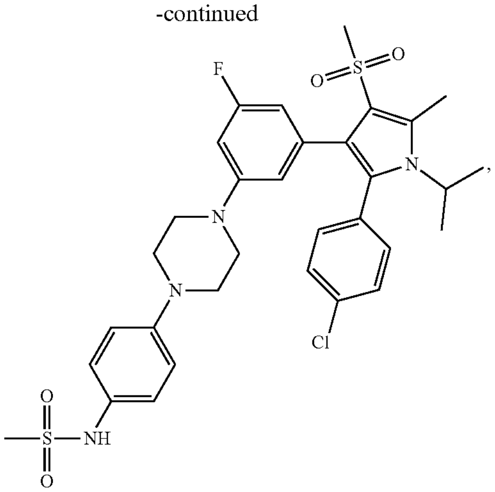

or a pharmaceutically acceptable salt thereof;

wherein Compound No. 1 or the pharmaceutically acceptable salt thereof is administered once weekly by intravenous administration at a weekly dosage about 160 mg; and (ii) osimertinib or a pharmaceutically acceptable salt thereof;

wherein the osimertinib or the pharmaceutically acceptable salt thereof is administered once daily by oral administration at a daily dosage of about 80 mg.

2. The method of claim 1, wherein the cancer is small cell lung cancer (SCLC), non-small cell lung carcinoma (NSCLC), or myelofibrosis.

3. The method of claim 1, wherein Compound No. 1 or the pharmaceutically acceptable salt thereof is administered three times in about every 21 days.

4. The method of claim 1, wherein Compound No. 1 or the pharmaceutically acceptable salt thereof is administered four times in about the first 28 days, and is administered three times in about every 28 days thereafter.

5. The method of claim 1, wherein Compound No. 1 or the pharmaceutically acceptable salt thereof is administered once weekly in about the first 28 days, and is administered once weekly for the first three weeks in about every 28 days thereafter.

6. The method of claim 1, wherein Compound No. 1 or the pharmaceutically acceptable salt thereof is intravenously administered for about 30 minutes weekly in about the first 28 days, and is intravenously administered for about 30 minutes weekly for the first three weeks in about every 28 days thereafter.

7. The method of claim 1, wherein a tablet of a mesylate salt of osimertinib is administered.

* * * * *